United States Patent
Lebron et al.

(10) Patent No.: US 11,399,986 B2
(45) Date of Patent: Aug. 2, 2022

(54) ARTICLE COMPRISING ENERGY CURABLE INK

(71) Applicant: The Procter & Gamble Company, Cincinnati, OH (US)

(72) Inventors: Ariel Lebron, Cincinnati, OH (US); John Ferrer, Mason, OH (US); John Andrew Strasemeier, Aurora, IN (US); Nicholas David Vetter, Cleves, OH (US); Alrick Vincent Warner, Loveland, OH (US); Paul Thomas Weisman, Cincinnati, OH (US); Hui Yang, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1053 days.

(21) Appl. No.: 15/831,416

(22) Filed: Dec. 5, 2017

(65) Prior Publication Data
US 2018/0168873 A1 Jun. 21, 2018

Related U.S. Application Data

(60) Provisional application No. 62/435,113, filed on Dec. 16, 2016.

(51) Int. Cl.
*A61F 13/15* (2006.01)
*A61F 13/514* (2006.01)
(Continued)

(52) U.S. Cl.
CPC .. *A61F 13/15203* (2013.01); *A61F 13/51394* (2013.01); *A61F 13/51496* (2013.01);
(Continued)

(58) Field of Classification Search
CPC ............... A61F 13/15203; A61F 13/42; A61F 13/51394; A61F 13/51496;
(Continued)

(56) References Cited

U.S. PATENT DOCUMENTS

| 3,465,350 A | 9/1969 | Keur et al. |
| 3,465,351 A | 9/1969 | Keur et al. |

(Continued)

FOREIGN PATENT DOCUMENTS

| EP | 0604729 | 7/1994 |
| WO | WO 9510996 | 4/1995 |

(Continued)

OTHER PUBLICATIONS

International Search Report, PCT/US2017/065694, dated Mar. 21, 2018, 15 pages.

*Primary Examiner* — Catharine L Anderson
(74) *Attorney, Agent, or Firm* — Sarah M. DeCristofaro

(57) ABSTRACT

A nonwoven substrate has a first surface and a second surface opposite the first surface. The first surface may include one or more printed portions, wherein at least one printed portion has a curable ink. Said printed portion may exhibit a Crosslinking Index of about 330 or less as determined by the Crosslinking Index Test Method herein and an IAR (Mineral Oil) of 1.30 or greater as determined by the IAR Test Method herein.

20 Claims, 6 Drawing Sheets

(51) Int. Cl.
   *A61F 13/513* (2006.01)
   *A61L 15/22* (2006.01)
   *B41J 2/21* (2006.01)
   *B41M 5/50* (2006.01)
   *C09D 11/101* (2014.01)

(52) U.S. Cl.
   CPC ............ *A61L 15/22* (2013.01); *B41J 2/21* (2013.01); *B41M 5/502* (2013.01); *C09D 11/101* (2013.01); *A61F 13/15585* (2013.01); *A61F 2013/15243* (2013.01); *A61F 2013/15406* (2013.01)

(58) Field of Classification Search
   CPC .. A61F 2013/15243; A61F 2013/15284; A61F 2013/422; A61F 2013/429; A61F 2013/51377; A61F 2013/8497
   See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 4,610,678 A | 9/1986 | Weisman et al. | |
| 4,662,875 A | 5/1987 | Hirotsu et al. | |
| 4,699,622 A | 10/1987 | Toussant et al. | |
| 4,846,815 A | 7/1989 | Molloy | |
| 4,854,984 A | 8/1989 | Ball et al. | |
| 4,892,536 A | 1/1990 | DesMarais et al. | |
| 4,894,060 A | 1/1990 | Nestegard | |
| 4,919,738 A | 4/1990 | Ball et al. | |
| 4,946,527 A | 8/1990 | Battrell | |
| 4,963,140 A | 10/1990 | Robertson et al. | |
| 4,990,147 A | 2/1991 | Freeland | |
| 5,037,416 A | 8/1991 | Allen et al. | |
| 5,137,537 A | 8/1992 | Herron et al. | |
| 5,151,092 A | 9/1992 | Buell et al. | |
| 5,221,274 A | 6/1993 | Buell et al. | |
| 5,242,436 A | 9/1993 | Weil et al. | |
| 5,260,345 A | 11/1993 | DesMarais et al. | |
| 5,266,392 A | 11/1993 | Bartz et al. | |
| 5,269,775 A | 12/1993 | Freeland et al. | |
| 5,340,648 A | 8/1994 | Rollins et al. | |
| 5,382,400 A | 1/1995 | Pike et al. | |
| 5,387,207 A | 2/1995 | Dyer et al. | |
| 5,397,316 A | 3/1995 | Lavon et al. | |
| 5,418,045 A | 5/1995 | Pike et al. | |
| 5,499,978 A | 3/1996 | Buell et al. | |
| 5,501,756 A | 3/1996 | Rollins et al. | |
| 5,507,736 A | 4/1996 | Clear et al. | |
| 5,507,909 A | 4/1996 | Rollins et al. | |
| 5,549,791 A | 8/1996 | Herron et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,152 A | 1/1997 | Buell et al. | |
| 5,607,760 A | 3/1997 | Roe | |
| 5,609,587 A | 3/1997 | Roe | |
| 5,622,772 A | 4/1997 | Stokes et al. | |
| 5,625,222 A | 4/1997 | Yoneda et al. | |
| 5,635,191 A | 6/1997 | Roe et al. | |
| 5,643,588 A | 7/1997 | Roe et al. | |
| 5,700,254 A | 12/1997 | McDowall et al. | |
| 5,707,468 A | 1/1998 | Arnold et al. | |
| 5,865,823 A | 2/1999 | Curro | |
| 6,004,306 A | 12/1999 | Robles et al. | |
| 6,077,375 A | 6/2000 | Kwok | |
| 6,107,537 A | 8/2000 | Elder et al. | |
| 6,120,487 A | 9/2000 | Buell et al. | |
| 6,132,411 A | 10/2000 | Huber et al. | |
| 6,200,635 B1 | 3/2001 | Kwok | |
| 6,235,137 B1 | 5/2001 | Van Eperen et al. | |
| 6,361,634 B1 | 3/2002 | White et al. | |
| 6,432,098 B1 | 8/2002 | Kline et al. | |
| 6,454,989 B1 | 9/2002 | Neely et al. | |
| 6,520,237 B1 | 2/2003 | Bolyard et al. | |
| 6,561,430 B2 | 5/2003 | Ou | |
| 6,582,518 B2 | 6/2003 | Riney | |
| 6,610,161 B2 | 8/2003 | Erdman | |
| 6,613,146 B2 | 9/2003 | Bolyard | |
| 6,632,386 B2 | 10/2003 | Shelley et al. | |
| 6,645,569 B2 | 11/2003 | Rohrbaugh et al. | |
| 6,652,693 B2 | 11/2003 | Burriss et al. | |
| 6,719,846 B2 | 4/2004 | Nakamura | |
| 6,737,102 B1 | 5/2004 | Saidman et al. | |
| 6,863,666 B2 | 3/2005 | Minato | |
| 6,863,933 B2 | 3/2005 | Rohrbaugh et al. | |
| 7,112,621 B2 | 9/2006 | Rohrbaugh et al. | |
| 7,291,239 B2 | 11/2007 | Polanco et al. | |
| 7,435,243 B2 | 10/2008 | Miyamoto | |
| 7,534,880 B2 * | 5/2009 | Norcini | C07C 45/46 544/106 |
| 7,786,341 B2 | 8/2010 | Schneider et al. | |
| 7,870,652 B2 | 1/2011 | Kline et al. | |
| 8,062,279 B2 | 11/2011 | Miyamoto | |
| 8,382,736 B2 | 2/2013 | Kline et al. | |
| 8,637,727 B2 * | 1/2014 | Maldonado | A61F 13/51496 604/361 |
| 8,690,852 B2 | 4/2014 | Macura et al. | |
| 8,728,051 B2 | 5/2014 | Lu et al. | |
| 8,939,957 B2 | 1/2015 | Ray et al. | |
| 8,979,815 B2 | 3/2015 | Roe et al. | |
| 8,992,499 B2 | 3/2015 | Kline et al. | |
| 9,060,904 B2 | 6/2015 | Hundorf et al. | |
| 9,072,634 B2 | 7/2015 | Hundorf et al. | |
| 9,211,356 B2 | 12/2015 | Gruenbacher et al. | |
| 9,301,889 B2 | 4/2016 | Miyamoto | |
| 9,358,161 B2 | 6/2016 | Lawson et al. | |
| 9,421,137 B2 | 8/2016 | Lavon et al. | |
| 9,532,908 B2 | 1/2017 | Wade et al. | |
| 2003/0148684 A1 | 8/2003 | Cramer et al. | |
| 2005/0008839 A1 | 1/2005 | Cramer et al. | |
| 2007/0118087 A1 | 5/2007 | Flohr et al. | |
| 2008/0091162 A1 | 4/2008 | Maldonado et al. | |
| 2008/0312622 A1 | 12/2008 | Hundorf et al. | |
| 2010/0040826 A1 | 2/2010 | Muslet et al. | |
| 2012/0316526 A1 | 12/2012 | Rosati et al. | |
| 2014/0274642 A1 | 9/2014 | Lavon et al. | |
| 2014/0276525 A1 | 9/2014 | Lavon et al. | |
| 2015/0015649 A1 | 1/2015 | Warner et al. | |
| 2015/0065973 A1 | 3/2015 | Roe et al. | |
| 2015/0126955 A1 | 5/2015 | Sauer et al. | |
| 2015/0159330 A1 * | 6/2015 | Weisman | D04H 1/4309 162/134 |
| 2016/0206483 A1 | 7/2016 | Nishikawa et al. | |
| 2016/0270972 A1 | 9/2016 | Surushe et al. | |
| 2016/0331601 A1 | 11/2016 | Lavon et al. | |

FOREIGN PATENT DOCUMENTS

| | | |
|---|---|---|
| WO | WO 9516746 | 6/1995 |
| WO | WO 9534329 | 12/1995 |
| WO | WO 200059430 | 10/2000 |
| WO | WO 02067809 | 9/2002 |
| WO | WO2016176244 | 11/2016 |

* cited by examiner

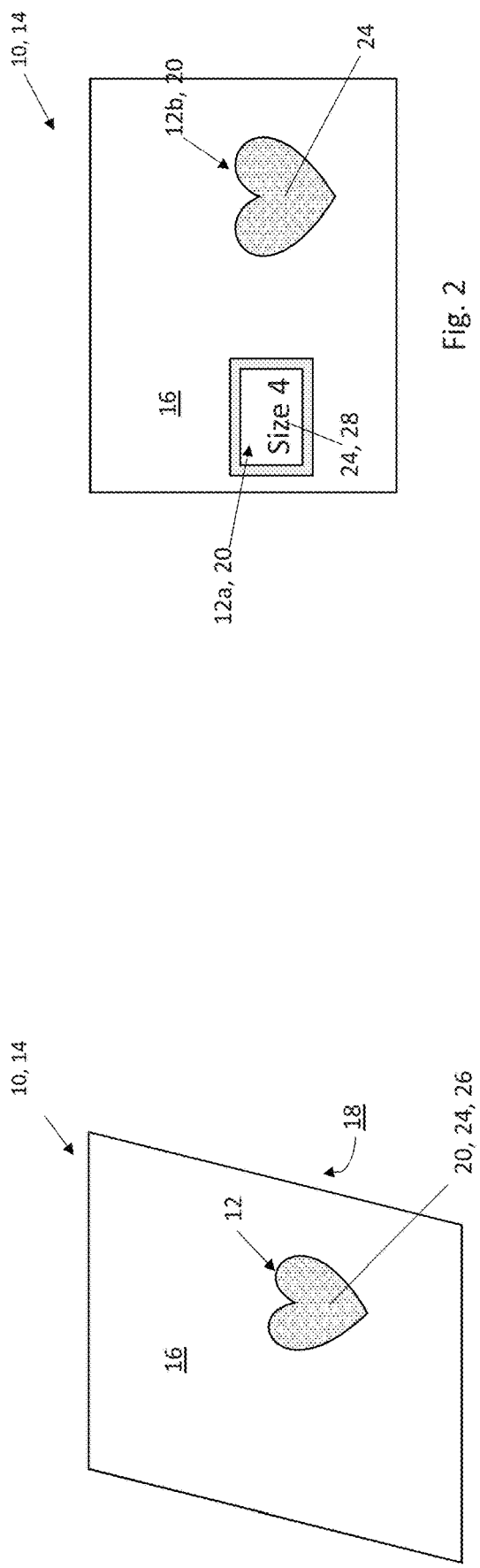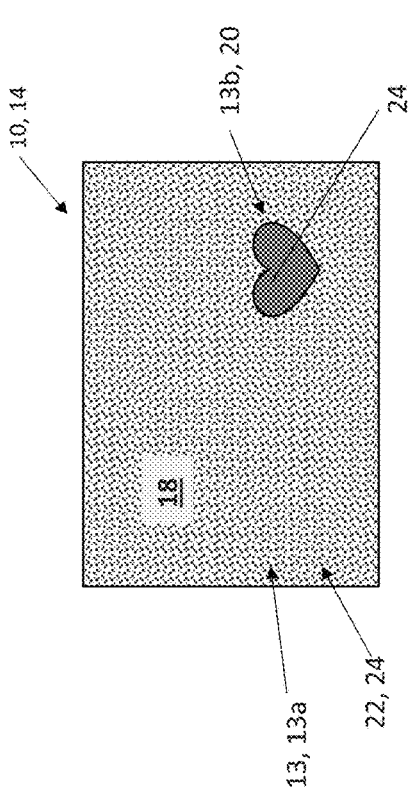

ARTICLE COMPRISING ENERGY CURABLE INK

FIELD OF THE INVENTION

The present invention relates to articles comprising energy curable inks, especially absorbent articles comprising energy curable inks.

BACKGROUND OF THE INVENTION

Many current products, such as diapers and training pants, include printed designs to improve their appearance. It is well known that consumers both appreciate and seek out absorbent articles that have colors or graphics. Manufacturers of absorbent products have delivered color and graphics in various ways. Most common is to use flexographic printing methods which rely on machined parts to construct a set graphic pattern. This printing method limits the flexibility of the manufacturer to provide a variety of graphics as changes are costly and time intensive to manufacture print plates. Flexographic printing most often requires manufacture at a different time than assembly of the end product (i.e., offline printing), which can increase costs.

Energy curable inks provide many desirable properties including enhanced visual appeal and the ability to digitally print such articles. Unlike traditional inks that dry, energy curable inks are solidified, polymerized, and/or crosslinked under exposure to ultraviolet, e-beam or other energy sources, which can allow printing during the assembly process (i.e., online print) thereby decreasing the overall time from printing the design to plant production of the assembled absorbent product and increasing efficiency of the overall delivery of a product with a new print design. Energy curable inks also provide for relatively easy changes in print designs and precision in graphics through digital and/or ink jet printing.

With such inks, sufficient curing is necessary to preclude ink rub off or other migration of ink components off of the product during use or processing. Indeed, depending on where the graphics are located on the absorbent articles, the printed ink could rub off onto clothing or skin. Thus, sufficient curing is paramount. Yet, balancing curing requirements with other needs can be difficult. Delivering vibrant graphics requires a sufficient amount of ink; however, a high basis weight of ink complicates the ability to sufficiently cure the ink. This is especially difficult when manufacturing at high speeds, such as is found with the manufacture of absorbent articles. Further, manufacturers often utilize porous substrates (e.g., nonwovens) in absorbent articles to provide desirable properties such as softness, durability and/or breathability. However, manufacturers have struggled with providing vibrant printing on such porous substrates, especially polyolefin based nonwovens and/or low basis weight nonwovens.

It is difficult to get high levels of curing on nonwovens at the high manufacturing rates of absorbent articles, while still delivering consumer desired levels of highly vibrant graphics which do not rub off, especially when the nonwoven encounters typical solvents, liquids, and/or conditions associated with the use and handling of absorbent articles.

Thus, there is a continued need for vibrant and/or high definition prints on nonwoven substrates. In addition, there is a need for printed substrates with little or no ink rub-off and/or migration of ink component materials. There is also a need for sufficient ink adhesion and ink penetration such that ink is highly visible, vivid and reflective of the intended design without bleeding through the substrate or rubbing off the surface of the printed substrate. Further, it would be desirable to solve these issues in a cost-effective and efficient manner, in particular for in manufacturing of disposable absorbent articles.

SUMMARY OF THE INVENTION

The present invention relates to printed substrates comprising energy curable inks. In some embodiments, the substrate comprises a nonwoven. The nonwoven substrate may comprise surface having a printed portion comprising curable ink. In certain embodiments, the printed portion comprises a Crosslinking Index of about 330 or less as determined by the Crosslinking Index Test Method herein and an IAR (Mineral Oil) of 1.30 or greater as determined by the IAR Test Method herein. In further embodiments, a printed portion may exhibit a Crosslinking Index of about 330 or less as determined by the Crosslinking Index Test Method herein and a $\Delta E^*$ of about 7 or greater as determined by the $\Delta E^*$ Determination Test Method herein. In still further embodiments, a printed portion may comprise a Crosslinking Index of about 330 or less, an IAR (Dry) of about 1.5 or greater, a $\Delta E^*$ of about 10 or greater, an Ink Penetration Depth of about 250 microns or less as determined by the Ink Penetration Test Method herein.

The printed substrates of the present invention may be included in absorbent articles, including but not limited to taped diapers, absorbent pants and feminine hygiene products.

BRIEF DESCRIPTION OF THE DRAWINGS

FIG. 1 is a schematic perspective view of a nonwoven substrate according to one nonlimiting embodiment of the present invention.

FIG. 2 is a schematic, plan view of a first surface of a nonwoven substrate according to another nonlimiting embodiment of the present invention.

FIG. 3 is a schematic, plan view of a second surface of a nonwoven substrate according to a nonlimiting embodiment of the present invention.

DETAILED DESCRIPTION OF THE INVENTION

Figure 4:
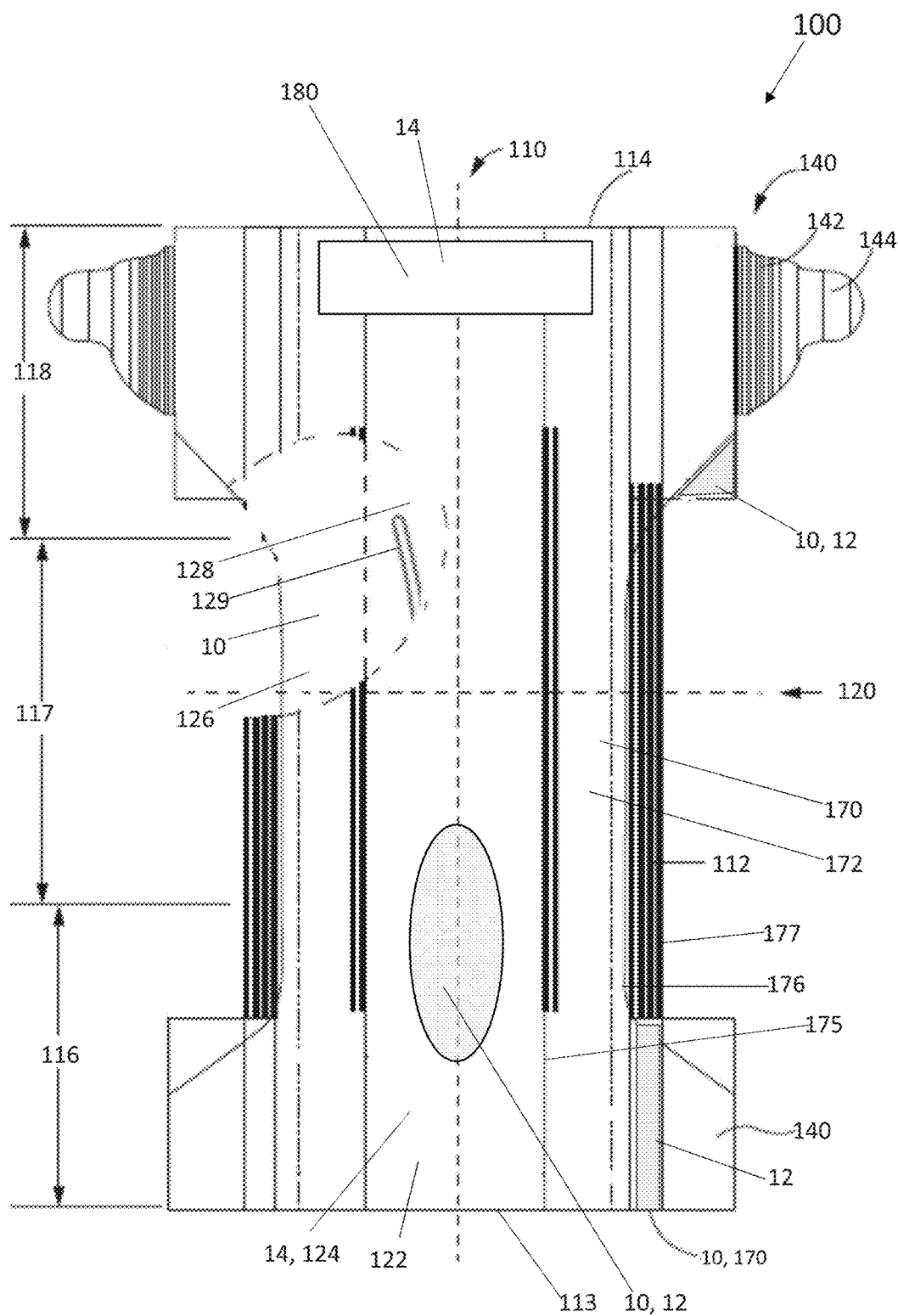
FIG. 4 is a schematic, plan view of an exemplary absorbent article according to one nonlimiting embodiment of the present invention. The absorbent article is shown in a flat, uncontracted state.

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Colorant" includes one or more of pigments and or dyes; colorant may further include an acrylic colloidal dispersion, acrylic solution, or surfactants and water.

"Design element" as used herein means a shape or combination of shapes that visually create a distinct and discrete component, regardless of the size or orientation of the component. A design element may be present in one or more patterns. A design element may be present one or more times within one pattern. In one nonlimiting example, the same design element is present twice in one pattern—the second instance of the design element is smaller than the first instance. One of skill in the art will recognize that alternative arrangements are also possible. Design elements may comprise insignia. Design elements and/or combinations of design elements may comprise letters, words and/or graphics such as flowers, butterflies, hearts, character representations and the like. Design elements and/or combinations of design elements may comprise instructional indicia providing guidance or instruction to the caregiver relative to placement and/or fit of the article about the wearer.

"Ink Basis Weight" as used herein is the weight per unit area of a sample reported in grams per square meter (gsm) and is measured according to the Ink Basis Weight Test Method described herein.

"Insignia" as used herein means objects, character representations, words, colors, shapes or other indicia that can be used to distinguish, identify or represent the manufacturer, retailer, distributor or brand of a product, including but not limited to trademarks, logos, emblems, symbols, designs, figures, fonts, lettering, crests or similar identifying marks.

"Film" means a sheet-like material wherein the length and width of the material far exceed the thickness of the material (e.g., 10×, 50×, or even 1000× or more). Films are typically liquid impermeable but may be configured to be breathable.

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal."

"Lateral" refers to a direction running from a longitudinal edge to an opposing longitudinal edge of the article and generally at a right angle to the longitudinal direction. Directions within 45 degrees of the lateral direction are considered to be "lateral."

"Nonwoven" means a porous, fibrous material made from continuous (long) filaments (fibers) and/or discontinuous (short) filaments (fibers) by processes such as, for example, spunbonding, meltblowing, airlaying, carding, coforming, hydroentangling, and the like. Nonwovens are fibrous substrates which do not have a woven or knitted filament pattern. Nonwovens may be liquid permeable or impermeable.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Pattern" as used herein means a decorative or distinctive design, not necessarily repeating or imitative, including but not limited to the following: clustered, geometric, spotted, helical, swirl, arrayed, textured, spiral, cycle, contoured, laced, tessellated, starburst, lobed, blocks, pleated, concave, convex, braided, tapered, and combinations thereof.

"Print resolution" as used herein is defined in terms of inkjet printing technology by Dots Per Inch (dpi), wherein dpi defines a density of dots of ink that can be printed across a one inch length of a substrate.

"Substrate" includes any material that the inks of the present invention can be printed on. Thus, substrates of the present invention include, but are not limited to nonwovens, fibrous polyolefin webs, cellulosic webs, laminates of one or more of the above or any combination of one or more of the above.

"Web" means a material capable of being wound into a roll. Webs may be films, nonwovens, laminates, apertured films and/or laminates, and the like. The face of a web refers to one of its two dimensional surfaces, as opposed to its edge.

"Machine direction" (MD) is used herein to refer to the direction of material flow through a process. In addition, relative placement and movement of material can be described as flowing in the machine direction through a process from upstream in the process to downstream in the process.

"Cross direction" (CD) is used herein to refer to a direction that is generally perpendicular to the machine direction.

Printed Substrate

The present invention relates to a substrate 10 having one or more printed portions 12 as shown in FIG. 1. In certain embodiments, the substrate 10 comprises a nonwoven substrate 14. In further embodiments, the nonwoven substrate 14 may comprise a polyolefin based nonwoven, including but not limited to nonwovens having polypropylene fibers and/or polyethylene fibers and/or bicomponent fibers comprising a polyolefin. Nonlimiting examples of suitable fibers include spunbond, spunlaid, meltblown, spunmelt, solventspun, electrospun, carded, film fibrillated, melt-film fibrillated, air-laid, dry-laid, wet-laid staple fibers, and other nonwoven web materials formed in part or in whole of polymer fibers as known in the art, and workable combinations thereof. Additionally or alternatively, the substrate may comprise a basis weight of at least about 8 gsm, or about 65 gsm or less, or from about 8 gsm to about 65 gsm, or from about 10 gsm to about 45 gsm, or from about 15 gsm to about 30 gsm, reciting for each range every 1 gsm increment therein. The substrate 10 may comprise a first surface 16 and a second surface 18, the second surface being substantially opposite the first surface 16.

The first surface 16 may comprise a printed portion 12, or multiple printed portions 12a, 12b as is shown in FIG. 2. Where the surface 16 comprises more than one printed portion, the printed portions 12a, 12b may comprise the same or different features; such features include the aggregate shape, dimensions, design elements, ink type and/or color, ink basis weight, Crosslinking Index, Ink Penetration Value, Ink Adhesion Rating, and ΔE*. The printed portions 12a, 12b may match in some embodiments. Matching does not require printed portions to be exactly the same; rather, the printed portions may comprise substantially similar design elements, which may be rotated, mirrored, reduced in size, enlarged in size and/or altered in aspect ratio between the printed portions and still be considered matching.

In some embodiments, the second surface 18 comprises one or more additional printed portions 13 as shown in FIG. 3. Where the surface 18 comprise more than one printed portion, the printed portions 13a, 13b may comprise the same or different features; such features include the aggregate shape, dimensions, design elements, ink type and/or color, ink basis weight, Crosslinking Index, Ink Penetration Value, Ink Adhesion Rating, and ΔE*. Likewise, a printed portion 12 on the first surface 16 may be the same as or may differ than the printed portion on a second surface. The printed portions 12, 13 on the two surfaces 16, 18 may overlap, partially overlap, or not overlap at all. In some embodiments, the printed portions 12, 13 on the two surfaces match and/or multiple printed portions 13a, 13b on the second surface 18 match.

Any printed portion 12, 13 may comprise one or more design elements 20, including but not limited to graphics, letters, instructional indicia, and insignia. In some embodiments, a printed portion 12, 13 comprises a pattern 22, as shown for example in FIG. 3 where the printed portion 13a comprises a pattern 22. The substrate 10 may be printed using ink jet printing in some embodiments.

At least one printed portion 12, 13 of the substrate may comprise an energy curable ink 24. It is also contemplated that traditional inks may be utilized on the substrate as well. Unlike traditional inks that dry when exposed to heat or ambient air for a given time, energy curable inks 24 undergo a chemical reaction when exposed to intense UV light or energy waves such as e-beam waves. For example, for a UV curable ink, a photochemical reaction causes monomers in the ink composition to polymerize and crosslink thereby affixing the ink 24 to a substrate 10 in a relatively short time.

The ink 24 may be deposited on the substrate by various printing methods, such as flexographic printing, rotogravure printing, screen-printing, inkjet printing, and the like. In certain embodiments, the ink is printed using inkjet printing. Inkjet printing is a non-impact dot-matrix printing technology in which droplets of ink are jetted from a small orifice in the printhead directly to a specified position on a substrate. Inkjet printheads may be configured to perform different types of inkjet printing, such as for example, "drop-on-demand" and "continuous" inkjet printing.

With "continuous" inkjet printing processes, an ink is supplied under pressure to an inkjet nozzle and forced out through a small orifice. Prior to passing out of the nozzle, the pressurized ink stream proceeds through a ceramic crystal, which is subjected to an electric current. The electric current causes a piezoelectric vibration equal to the frequency of an AC electric current. The vibration, in turn, generates the ink droplets from the unbroken ink stream. As such, the ink stream breaks up into a continuous series of drops which are equally spaced and of equal size. Surrounding the jet, at a point where the drops separate from the fluid stream in a charge electrode, a voltage is applied between the charge electrode and the drop stream. When the drops break off from the stream, each drop carries a charge proportional to the applied voltage at the instant at which it breaks off. By varying the charge electrode voltages at the same rate as drops are produced, it is possible to charge every drop to a predetermined level. The drop stream passes between two deflector plates which are maintained at a constant potential that deflects a drop towards one of the plates by an amount proportional to the charge carried. Drops that are uncharged are undeflected and collected into a gutter to be recycled to the ink nozzle. Those drops which are charged, and hence deflected, impinge on a substrate traveling at a high speed at right angles to the direction of drop deflection. By varying the charge on individual drops, a desired pattern, design element etc. can be printed.

With "drop-on-demand" inkjet printing processes, an ink is forced under pressure from the printhead through a relatively small orifice in the form of minute droplets by rapid pressure impulses. In some configurations, the orifice may have a diameter of about 0.0024 inches (5-50 microns). The rapid pressure impulses may be generated in the printhead by either expansion of a piezoelectric crystal vibrating at a high frequency or volatilization of a volatile composition (e.g. solvent, water, propellant) within the ink by rapid heating cycles. The piezoelectric crystal expansion causes the ink to pass through the orifice as minute droplets in proportion to the number of crystal vibrations. Thermal inkjet printers employ a heating element within the printhead to volatilize a portion of the composition that propels the vast majority of fluid through the orifice nozzle to form droplets in proportion to the number of on-off cycles for the heating element. The ink is forced out of the nozzle when needed to print a spot on a substrate as part of a desired image. The minute droplets may also be energized to achieve an electrical charge and deflected as in the continuous inkjet printing process discussed above. Various inkjet printing processes are more particularly described in U.S. Pat. Nos. 3,465,350; 3,465,351; and 9,211,356.

A nonlimiting example of a method and/or apparatus for printing substrates herein is disclosed in U.S. Pat. App. No. 62/304,292.

In further embodiments, the ink 24 may have a basis weight of at least about 0.5 gsm, or at least about 1.0 gsm, or at least about 1.5 gsm, or from about 1 gsm to about 7 gsm, or about 1.5 gsm to about 5.5 gsm, or about 6 gsm or less. The ink 24 may have a print resolution of at least about 64 dpi, or at least about 100 dpi, or from about 64 dpi to about 1200 dpi, or from about 200 to about 400 dpi, or about 400 dpi or less, reciting for each range every 1 dpi increments therein and all ranges formed therein or thereby in the cross machine direction of the substrate, which in some embodiments corresponds to the lateral direction of the substrate. The ink 24 may have a print resolution of at least about 10 dpi, or about 6000 dpi or less, or about 1500 dpi or less, or about 100 dpi or less, or from about 10 dpi to about 6000 dpi, reciting for each range every 1 dpi increments therein and all ranges formed therein or thereby in the machine direction of the substrate, which in some embodiments corresponds to the longitudinal direction of the substrate.

The ink 24 may comprise a colorant. In some embodiments, the ink 24 comprises cyan, magenta, yellow, black or combinations thereof. The ink 24 may be disposed in a design element 20 as illustrated in FIGS. 1-3 for example. Additionally, or alternatively, the ink 24 may be disposed in a pattern 22. In some embodiments, however, the ink 24 is disposed such that there is no discernable pattern in the printed portion. The ink 24 may be disposed on at least 5%, or at least 10%, or at least 20%, or at least 25%, or from about 10% to about 90% of the surface based on the total area of the surface as determined by the Percent Printed Color Area Test Method herein. The colorant has no significant effect with respect to Crosslinking Index, Ink Adhesion Ratings, ΔE* or Ink Penetration, and the values of said properties disclosed herein can be achieved with various colorants.

In certain embodiments, the energy curable ink 24 comprises an electron beam energy curable ink 26 (hereinafter referred to as an e-beam ink) as illustrated in FIG. 1. E-beam inks 26 are cured by electron irradiation at a dosage suitable to result in curing the ink to the substrate. Nonlimiting examples of suitable doses of electron irradiation experienced by the substrate and ink include from about 0.5 MRads to about 10 MRads, or from about 1 MRad to about 5 MRads, reciting for each range every 1 increment therein. Nitrogen gas ($N_2$) may be used to facilitate the curing process to ensure maximal energy is directed to the ink. Without being bound by theory, it is believed different levels of electron irradiation may be used depending on factors such as curing time, substrate type (e.g., nonwoven or other substrate), ink composition, and/or amount of ink. The inventive combination of factors as taught herein yields desired crosslinking index levels and/or other desirable properties. Nonlimiting examples of suitable e-beam inks 26 are available from Wikoff Color Corp. of Fort Mill, S.C. under product codes 3.860.4.015252/SCIJ-15252 Free EB Inkjet Black, 3.860.4.015253/SCIJ-15253 Free EB Inkjet Cyan, 3.860.4.015252/SCIJ-15255 Free EB Inkjet Yellow, or 3.860.4.015254/SCIJ-15254 Free EB Inkjet Magenta.

In further embodiments, the energy curable ink 24 may comprise an ultraviolet curable ink 28 (hereinafter referred to as an UV ink 28) as illustrated in FIG. 2. UV curable inks 28 are cured by exposure to ultraviolet waves, typically in the range of from about 200 nm to about 400 nm, or from about 300 nm to about 400 nm, reciting for each range every 10 nm increment therein. In nonlimiting examples, UV inks 28 are cured using a 365 nm wavelength or a 395 nm wavelength. Any suitable wavelength may be utilized. UV inks 28 incorporate one or more photoinitiators to trigger the crosslinking polymerization. In nonlimiting examples, an UV ink 28 comprises about 15% or less, or about 10% or less by weight of photoinitiator(s). The type of photoinitiator may affect the wavelength necessary for curing. UV inks 28 may be cured using energy dosage of at least about 10 $mJ/cm^2$, or about 2000 $mJ/cm^2$ or less, or about 1000 $mJ/cm^2$ or less, from about 10 $mJ/cm^2$ to about 2000 $mJ/cm^2$, or from about 25 $mJ/cm^2$ to about 1000 $mJ/cm^2$, reciting for each range every 10 $mJ/cm^2$ increment therein. In further nonlimiting examples, LED lamps may be used during the curing process. Without being bound by theory, it is believed different levels of energy and/or different wavelengths may be used depending on factors such as curing time, substrate type (i.e., nonwoven or other substrate), ink composition, and/or amount of ink. The inventive combination of factors as taught herein yields desired crosslinking index levels and/or other desirable properties. Nonlimiting examples of suitable UV inks are available from Kao Collins Inc. of Cincinnati, Ohio under the product codes/categories: Jet LED Platform, PUC250454 cyan, PUC261754 cyan, PUC262154 LIGHT cyan, PUY250654 yellow, PUY261954 yellow, PUM250554 magenta, PUM261854 magenta, PUM262054 light magenta, PUK1176 black, PUK250754 black, or PUR242158 red (PMS 032), Flex UV Platform, Jet UV Platform, LOK UV Platform, Stretch UV Platform, PUB242359 blue (PMS 3025), PUG249652 green (PMS 347), or PUK1189 black.

In certain embodiments, the ink 24 may be in the form of a hybrid composed of energy curable ingredients in an aqueous solution. In some configurations, a multi-stage printing system may be utilized. In some configurations, to improve ink rub-off resistance, ink compositions used herein may contain a wax. Such waxes may include a polyethylene wax emulsion. Addition of a wax to the ink composition may enhance rub resistance by setting up a barrier which inhibits the physical disruption of the ink film after application of the ink to the fibrous sheet. Based on weight percent solids of the total ink composition, addition ranges for the wax may be from about 0.5% solids to 10% solids. An example polyethylene wax emulsion is JONWAX 26 supplied by S.C. Johnson & Sons, Inc. of Racine, Wis.

In previous attempts to utilize curable inks, manufacturers faced a number of drawbacks. For example, printed substrates included residual component materials which failed to completely cure, lacked clarity and vibrancy and/or were prone to rub-off. Manufacturers found one desirable characteristic had to be compromised in order to achieve another. For instance, the low surface energy of nonwovens (especially polyolefin fiber nonwovens) typically counteracts ink adhesion. Likewise, to deliver vibrant graphics requires a sufficient amount of ink; however a high basis weight of ink complicates the ability to sufficiently cure the ink, especially at high manufacturing speeds. The present invention overcomes drawbacks in that the ink on the printed portion may comprise a Crosslinking Index of about 330 or less (which signifies low residuals of acrylate monomer(s)) while maintaining consumer acceptable adhesion, color clarity and/or ink penetration. Without being bound by theory, it is believed the characteristics described herein may be achieved through a combination of curing conditions, substrate type (e.g., nonwoven or other substrate), ink composition, and/or amount of ink.

Optionally, the ink 24 may be compounded to be printed to meet select physical property ranges. While not wishing to be bound by theory, it is believed certain physical property ranges may enhance the characteristics of the printed portion 12, 13. In one nonlimiting example, the ink 24 may have a surface tension so as when compared to the surface tension of the substrate 10 surfaces 16, 18 is lower thereby promoting the wetting of the substrate 10 by the ink 24. In another example, the ink 24 may have a viscosity so upon wetting the substrate or nonwoven it thereby promotes ink penetration therein. In yet another example, the ink 24 may have a specific gravity so as to be relatively heavy and also promote wetting of the substrate 10 and thereby promoting ink penetration therein.

In some embodiments, the ink composition may have a relatively low surface tension compared to the surface tension of the fibers making up the substrate 10, such as fibers in a nonwoven 14, or surfaces 16, 18 of the substrate, so as facilitate wetting by the ink composition. The surface tension may provide desirable ink wetting of the substrate. In one nonlimiting example, the ink composition may have a surface tension as measured in dyne/cm at 25 degrees Celsius, which is numerically less than the surface tension of the fibers or surfaces making up the substrate, such as a nonwoven. In yet another example, the ink composition may have a surface tension as measured in dyne/cm at 25 degrees Celsius of less than 30.

In some embodiments, the ink composition may have a viscosity such that ink penetration occurs upon wetting the substrate 10. It is to be appreciated that various factors may influence ink penetration, such as for example, the ink's resistance to flow, thickness, and/or viscosity. In accordance with one embodiment, the ink composition may have a viscosity in the range of 1 to 30 millipascal seconds. The viscosity measurement is done according to ASTM D 2196-99 Test Method A, where a UL adaptor is utilized and the measurements are made as outlined in ASTM D 2196-99, Test Method A at 25° C. and 60 rpm. Shake time and spindle selection are as indicated within the test method.

In some embodiments, it may be desired to utilize an ink 24 having a specific gravity that also promotes wetting of the substrate or nonwoven and thereby promoting ink penetration therein. An example ink composition may have a specific gravity in the range of 0.830 to 1.050. The specific gravity is measured according to ASTM D 891-95 following Method A and determined at 25° C.

In some embodiments, the ink 24 may include a solvent. In some examples, solvents and/or solvent blends may be used to achieve or help achieve desired physical properties, surface tension, viscosity, or specific gravity or a combination thereof. Suitable solvents for ink composition may include, without limitation, alcohols, acetates, ketones, glycol ethers, aromatic hydrocarbons, aliphatic naphthas, water, glycols, and combinations thereof. As an example, suitable alcohols include ethyl alcohol, isopropyl alcohol, N-propyl alcohol, and blends thereof. Suitable acetates include ethyl acetate, N-propyl acetate, N-butyl acetate, isopropyl acetate, isobutyl acetate, butyl acetate, and blends thereof. Suitable glycol ethers include ethylene glycol monopropyl ether, ethylene glycol monobutyl ether, diethylene glycol monomethyl ether, diethylene glycol monopropyl ether, propylene glycol monomethyl ether, polyproylene glycol n-propyl ether, and blends thereof. As another example, suitable solvents include dipropylene glycol methyl ether, dipropylene glycol n-butyl ether, propolyene glycol, ethylene glycol, dipropylene glycol, and combinations or blends thereof.

In some embodiments, at least one printed portion 12, 13 comprises a Crosslinking Index of about 330 or less, or about 200 or less, or from about 10 to about 330, or from about 25 to about 200, or from about 10 to about 100, reciting for each range every 10 increment therein. In nonlimiting examples, a printed portion comprising an e-beam ink 26 exhibits a Crosslinking Index of about 350 or less, or about 330 or less, or about 100 or less, or about 10 to about 330, or from about 10 to about 100, reciting for each range every 10 increment therein. In further nonlimiting examples, a printed portion comprising an UV ink 28 exhibits a Crosslinking Index of about 250 or less, or about 200 or less, or about 190 or less, or from about 25 to about 200, reciting for said range every 10 increment therein.

In certain embodiments, at least one printed portion 12, 13 comprises an Ink Adhesion Rating (hereinafter IAR) of about 0.5 or greater, or about 1 or greater, or about 1.3 or greater, or about to 2 or greater, or about 2.3 or greater, from about 0.5 to about 5, or from about 1 to about 4.5, reciting for each range every 0.2 increment therein, in accordance with the Ink_Adhesion Rating Test Method herein. The printed portion may comprise an IAR (Mineral Oil) of about 1 or greater, or about 1.3 or greater, or about 1 to about 4.5, or about 1.3 to about 4.5, reciting for each range every 0.1 increment therein. A printed portion comprising a UV ink 28 may comprise an IAR (Mineral Oil) of about 1 or greater, or about 2 or greater, or about 2.5 or greater, or from about 2 to about 4.5, or from about 2.3 to about 4.2, reciting for each range every 0.1 increment therein. A printed portion comprising an e-beam ink 26 may exhibit an IAR (Mineral Oil) of about 1 or greater, or about 1.3 or greater, or about 1.5 or greater, or about 2 or greater, or from about 1 to about 2.5, or from about 1.3 to about 2.3, reciting for each range every 0.1 increment therein. At least one printed portion 12, 13 may comprise an IAR(Synthetic Urine) of about 2 or greater, or about 3 or greater, or from about 2 to about 5, or from about 2.1 to about 4.8, reciting for each range every 0.1 increment therein, in accordance with the Ink Adhesion Rating Test Method herein. A printed portion comprising UV ink 28 may exhibit an IAR(Synthetic Urine) of about 3 or greater, or about 3.5 or greater, or about 3.8 or greater, or from about 3 to about 5, or from about 3.5 to about 4.8, reciting for each range every 0.1 increment therein. A printed portion comprising an e-beam ink 26 may exhibit an IAR(Synthetic Urine) of about 2 or greater, or about 3 or greater, or 3.4 or greater, or from about 1.5 to about 4, or from about 2 to about 3.8, reciting for each range every 0.1 increment therein.

At least one printed portion 12, 13 may comprise an IAR (Dry) of about 1 or greater, or about 1.5 or greater, or about 3 or greater, or from about 1 to about 5, or from about 1.5 to about 4.7, reciting for each range every 0.1 increment therein, in accordance with the Ink Adhesion Rating Test Method herein. A printed portion comprising a UV ink 28 may exhibit an IAR (Dry) of about 3 or greater, or about 4 or greater, or from about 3 to about 5, or from about 4 to about 4.7, reciting for each range every 0.1 increment therein. A printed portion comprising e-beam ink 26 may exhibit an IAR (Dry) of about 1.5 or greater, or about 3 or greater, or about 3.5 or greater, from about 1.0 to about 4.5, reciting for said range every 0.1 increment therein. The aforementioned IAR values may be present in combination with any of the ink or substrate properties disclosed herein, including but not limited to the Crosslinking Index values, and/or basis weight values.

In certain embodiments, at least one printed portion 12, 13 comprises an ΔE* of about 7 or greater, or about 10 or greater, or about 12 or greater, or from about 10 to about 50, or from about 12 to about 35 as determined by the ΔE* Determination Test Method herein, reciting for each range every 2 increment therein. A printed portion comprising an e-beam ink 26 may exhibit an ΔE* of about 15 or greater, of about 20 or greater, or from about 15 to about 30, or from about 20 to about 25, reciting for each range every 0.1 increment therein. A printed portion comprising a UV ink 28 may exhibit a ΔE* of about 10 or greater, or about 12 or greater, or from about 10 to about 50, or from about 12 to about 35. The aforementioned ΔE* values may be present in combination with any of the ink or substrate properties described herein, including but not limited to Crosslinking Index values, IAR values, and/or basis weight values.

In further embodiments, at least one printed portion 12, 13 comprises an Ink Penetration Depth of about 300 microns or less, or about 250 microns or less, or about 230 microns or less as determined by the Ink Penetration Depth Test Method herein. A printed portion comprising an e-beam ink 26 may comprise an Ink Penetration Depth of about 250 microns or less, or about 230 microns or less, or about 225 microns or less. A printed portion comprising a UV ink 28 may comprise an Ink Penetration Depth of about 215 microns or less, or about 210 microns or less, or about 205 microns or less. Without being bound by theory, it is believed that Ink Penetration Depths as prescribed result in the ink 24 not flowing too far into the substrate 10, and thereby the ink remains susceptible to curing energy. Further, it is believed the ink 24 at such penetration depths is able to better reflect light and exhibit greater vibrancy and optical density. Inks having any of the properties described herein, including but not limited to Crosslinking Index values, IAR values, and/or ink basis weight values, may have the aforementioned Ink Penetration Depths.

Table 1 shows six e-beam samples, cured at various energy levels on a nonwoven substrate, having a basis weight of 25 gsm and formed from polypropylene/polypropylene bicomponent fibers. Each sample was printed with an e-beam curable, cyan ink available from Wikoff Color Corp. under the product code 0.860.4.015253/SCIJ-15253 Free EB Inkjet Cyan. Each sample had approximately the same ink basis weight of about 3.5 gsm. As can be seen from the table, a Crosslinking Index of about 330 or less was achieved in presence of nitrogen gas to facilitate curing and also in absence of nitrogen gas when assisted by high energy levels. Further, desirable low Crosslinking Index values can be achieved at various electron irradiance levels while obtaining an IAR of about 1.3 or greater, or about 2 or greater, or about 3 or greater. Likewise, a ΔE* of about 20 or greater is achievable while maintaining a low Crosslinking Index.

TABLE 1

| Sample | E-beam Energy (MRads) & N₂ presence | Ink Basis Weight (gsm) | ΔE* | Cross-linking Index | IAR (Dry) | IAR (SynU) | IAR (MO) |
|---|---|---|---|---|---|---|---|
| EB 1 | 5 with N₂ | 3.51 | 23.3 | 10.3 | 4.7 | 4.7 | 3.6 |
| EB 2 | 4 with N₂ | 3.51 | 25.9 | 12.8 | 4.6 | 4.7 | 3.6 |
| EB 3 | 3 with N₂ | 3.51 | 24.0 | 26.9 | 4.3 | 4.6 | 3.6 |
| EB 4 | 2 with N₂ | 3.51 | 24.9 | 37.6 | 4.4 | 4.5 | 3.8 |
| EB 5 | 1 with N₂ | 3.51 | 25.1 | 91.0 | 4.1 | 4.6 | 2.9 |
| EB 6 | 5 without N₂ | 3.51 | 20.5 | 330.5 | 1.5 | 2.1 | 1.3 |

Table 2 shows ten UV samples cured at various energy dosages on a nonwoven substrate having a basis weight of 25 gsm and formed from polypropylene/polypropylene bicomponent fibers. Each sample was printed with a UV LED curable, cyan ink available from Kao Collins under the product code PUC250454. Each UV sample had approximately the same basis weight of about 1.5 gsm. The samples were cured under a LED lamp with a 395 nm wavelength. As shown in Table 2, a Crosslinking Index of about 60 or less, or about 56 or less, can be achieved at various energy dosages while maintaining an IAR of about 2 or greater, or about 2.3 or greater, or about 3 or greater, or about 4 or greater, even at a relatively low ink basis weight. Further, a ΔE* of about 10 or greater, or about 12 or greater can be achieved in combination with a low Crosslinking Index.

TABLE 2

| Sample | 395 nm UV LED Energy (mJ/cm²) | Ink Basis Weight (gsm) | ΔE* | Cross-linking Index | IAR (Dry) | IAR (SynU) | IAR (MO) |
|---|---|---|---|---|---|---|---|
| UV 1 | 169 | 1.49 | 12.5 | 48.5 | 4.3 | 3.9 | 2.4 |
| UV 2 | 246 | 1.51 | 13.5 | 24.7 | 4.4 | 4.1 | 2.3 |
| UV 3 | 282 | 1.49 | 12.6 | 54.7 | 4.3 | 4.1 | 2.5 |
| UV 4 | 390 | 1.55 | 13.0 | 32.0 | 4.4 | 4.0 | 2.3 |
| UV 5 | 674 | 1.52 | 12.1 | 30.9 | 4.4 | 4.1 | 2.6 |
| UV 6 | 168 | 1.48 | 13.8 | 49.2 | 4.4 | 3.9 | 2.5 |
| UV 7 | 246 | 1.50 | 14.3 | 55.7 | 4.3 | 4.0 | 2.8 |
| UV 8 | 281 | 1.50 | 13.8 | 39.1 | 4.4 | 3.8 | 2.3 |
| UV 9 | 387 | 1.51 | 13.4 | 42.0 | 4.4 | 4.0 | 2.4 |
| UV 10 | 675 | 1.50 | 14.1 | 38.4 | 4.3 | 3.9 | 2.1 |

Table 3 shows twelve UV samples on a nonwoven substrate, having a basis weight of 25 gsm and formed from polypropylene/polypropylene bicomponent fibers. The samples were cured at various energy dosages and were printed at different ink basis weights. Each sample was cured under a LED lamp with a 395 nm wavelength. As is shown in Table 3, using the basis weights and energy dosages in the disclosed ranges, a low Crosslinking Index can be achieved in combination with a desirable IAR and/or ΔE*. Indeed, a Crosslinking Index of about 200 or less, or about 195 or less, or about 100 or less, or about 35 to about 200, or about 40 to about 195, reciting for each range every 10 increment therein, can be achieved while maintaining a IAR of about 1.3 or greater, or about 2.5 or greater, or about 3 or greater, or about 3.5 or greater. Likewise, a ΔE* of about 12 or greater, or about 13.5 or greater, or about 20 or greater, or about 30 or greater can be achieved in combination with a low Crosslinking Index.

TABLE 3

| Sample | 395 nm UV LED Energy (mJ/cm²) | Ink Basis Weight (gsm) | ΔE* | Cross-linking Index | IAR (Dry) | IAR (SynU) | IAR (MO) |
|---|---|---|---|---|---|---|---|
| UV11 | 200 | 5.56 | 33.3 | 79.4 | 3.1 | 2.9 | 2.0 |
| UV12 | 200 | 3.56 | 24.3 | 59.3 | 3.3 | 3.2 | 2.0 |
| UV13 | 200 | 1.5 | 14.9 | 49.9 | 3.9 | 3.3 | 2.3 |
| UV14 | 100 | 5.56 | 33.5 | 109.3 | 3.1 | 2.7 | 1.8 |
| UV15 | 100 | 3.56 | 24.5 | 73.9 | 3.1 | 3.2 | 1.7 |
| UV16 | 100 | 1.5 | 15.7 | 40.7 | 3.7 | 3.5 | 2.0 |
| UV17 | 50 | 5.56 | 31.7 | 138.6 | 3.1 | 2.4 | 1.5 |
| UV18 | 50 | 3.56 | 24.6 | 83.2 | 3.1 | 2.4 | 1.7 |
| UV19 | 50 | 1.5 | 15.3 | 51.2 | 3.6 | 3.4 | 2.0 |
| UV20 | 25 | 5.56 | 29.8 | 191.5 | 2.6 | 2.4 | 1.3 |
| UV21 | 25 | 3.56 | 22.5 | 157.4 | 3.1 | 2.6 | 1.4 |
| UV22 | 25 | 1.5 | 13.5 | 82.0 | 3.5 | 3.5 | 2.0 |

Table 4 shows seven samples with energy curable inks including four e-beam inks and three UV inks, each cured on a nonwoven substrate having a basis weight of 25 gsm and formed from polypropylene/polypropylene bicomponent fibers. The inks are provided at various basis weights and cured at various energy levels. Table 4 shows that inks of different basis weights were able to be sufficiently cured, with an Ink Penetration Depth of about 225 microns or less, ensuring a vibrant appearance of the printed portion. Further, such Ink Penetration Depth can be achieved in combination with a low Crosslinking Index, such as a Crosslinking Index of about 330 or less, or about 100 or less, or about 50 or less. Further still, the Ink Penetration Depth can be achieved in combination with an IAR of about 1.3 or greater, or about 2.4 or greater, or about 3 or greater.

TABLE 4

| Sample | E-Beam Energy (MRads) & N$_2$ presence | 395 nm UV LED Energy (mJ/cm$^2$) | Ink Basis Weight (gsm) | ΔE* | Crosslinking Index | IAR(Dry) IAR(SynU) IAR(MO) | Ink Penetration Depth (μm) |
|---|---|---|---|---|---|---|---|
| EB 1 | 5 with N$_2$ | n/a | 3.51 | 23.3 | 10.3 | 4.7 / 4.7 / 3.6 | 195 |
| EB 4 | 2 with N$_2$ | n/a | 3.51 | 24.9 | 37.6 | 4.4 / 4.5 / 3.8 | 202 |
| EB 5 | 1 with N$_2$ | n/a | 3.51 | 25.1 | 91.0 | 4.1 / 4.6 / 2.9 | 218 |
| EB 6 | 5 without N$_2$ | n/a | 3.51 | 20.5 | 330.5 | 1.5 / 2.1 / 1.3 | 223 |
| UV 1 | n/a | 169 | 1.49 | 12.5 | 48.5 | 4.3 / 3.9 / 2.4 | 196 |
| UV 4 | n/a | 390 | 1.55 | 13.0 | 32.0 | 4.4 / 4.0 / 2.3 | 205 |
| UV 5 | n/a | 674 | 1.52 | 12.1 | 30.9 | 4.4 / 4.1 / 2.6 | 199 |

Articles Comprising the Printed Substrate

The printed substrate 10 may be incorporated into an absorbent article 100, which may be disposable. FIG. 4 is a plan view of an exemplary, non-limiting embodiment of an absorbent article 100 of the present invention in a flat, uncontracted state. The body-facing surface of the absorbent article 100 is facing the viewer. The absorbent article 100 includes two longitudinal edges 112, a front waist edge 113 opposite a back waist edge 114, and a longitudinal centerline 110 and a lateral centerline 120. The absorbent article 100 comprises a chassis 122. The absorbent article 100 and chassis 122 are shown to have a first waist region 116, a second waist region 118 opposed to the first waist region 116, and a crotch region 117 located between the first waist region 116 and the second waist region 118. The waist regions 116 and 118 generally comprise those portions of the absorbent article 100 which, when worn, encircle the waist of the wearer. The crotch region 117 is the portion of the absorbent article 100 which, when the absorbent article 100 is worn, is generally positioned between the legs of the wearer.

The chassis 122 may comprise a liquid permeable topsheet 124, a backsheet 126, and an absorbent core 128 between the topsheet 124 and the backsheet 126. The topsheet 124 may be joined to the core 128 and/or the backsheet 126. The backsheet 126 may be joined to the core 128 and/or the topsheet 124. It should be recognized that other structures, elements, or substrates may be positioned between the core 128 and the topsheet 124 and/or backsheet 126, including but not limited to an acquisition-distribution system. In certain embodiments, the chassis 122 comprises the main structure of the absorbent article 100 with other features added to form the composite absorbent article structure. While the topsheet 124, the backsheet 126, and the absorbent core 128 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

Figure 7B:
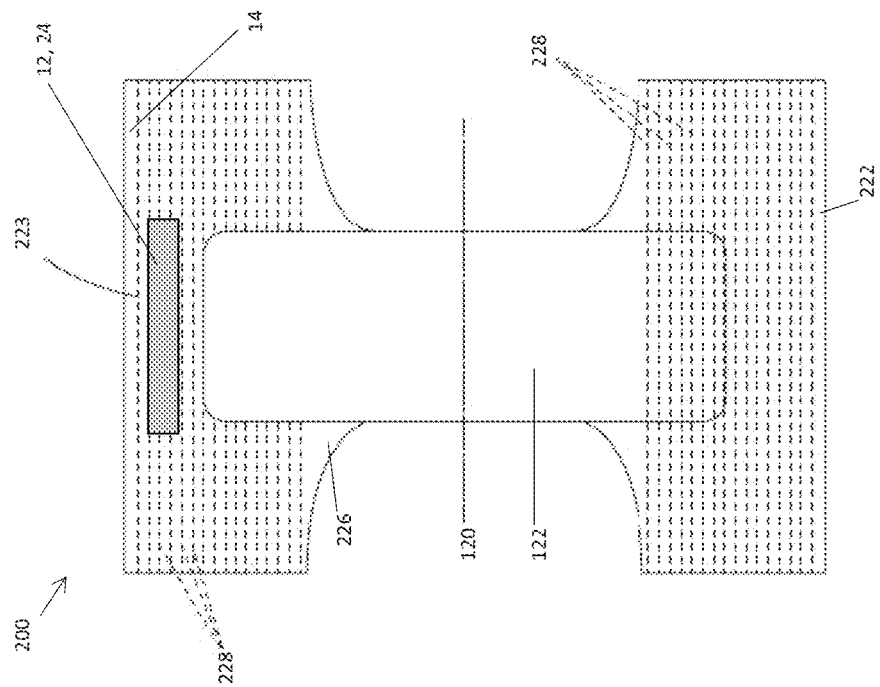
FIG. 7b is a schematic plan view of an exemplary absorbent pant precursor structure, prior to joining of the front and rear sections of the belt.
Figure 7A:
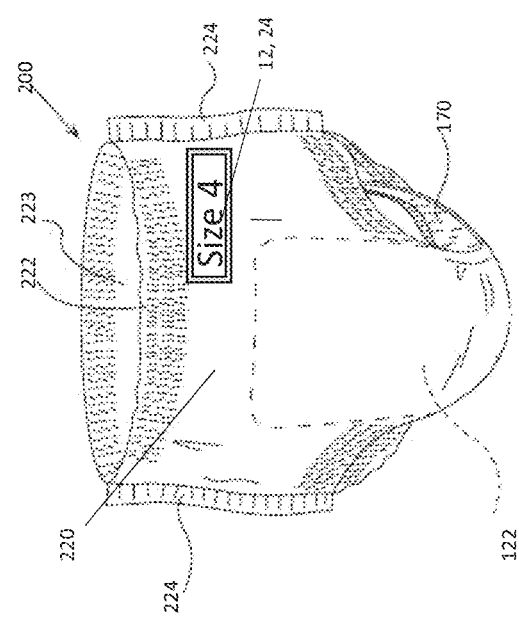
FIG. 7a is a perspective view of an exemplary absorbent pant according to one nonlimiting embodiment of the present invention.

The article 100 may comprise a component having the printed substrate 10 which has an energy curable ink 24. The substrate 10 may be disposed in one of the first waist region, second waist region, and/or crotch region. The substrate 10 may comprise a nonwoven 14. Further, the substrate may comprise printed portions 12, 13 on one or both surfaces 16, 18. The energy curable ink 24 may comprise any of the characteristics described herein. Nonlimiting examples of components comprising the substrate include the topsheet 124, the backsheet 126, a leg cuff 172, an ear 140, a landing zone 146, a waist feature 180 and a belt 220 as is illustrated in FIGS. 4 and 7a-7b. In some embodiments, the ink 24 may be disposed on at least 5%, or at least 10%, or at least 20%, or at least 25%, or from about 10% to about 90% of a surface of the component based on the total area of the surface of said component as determined by the Percent Printed Color Area Test Method herein.

Topsheet:

The topsheet 124 may be positioned at least in partial contact or close proximity to a wearer. Suitable topsheets 124 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. In certain embodiments, the topsheet 124 comprises a nonwoven 14. In further embodiments, the topsheet 124 comprises one or more printed portions 12 as exemplified in FIG. 4. Said printed portions 12 may comprise an energy curable ink 24, which may be disposed in one or more patterns 22 and/or design elements 20 including but not limited to graphics, instructional indicia, and insignia. The topsheet 124 is generally supple, soft feeling, and non-irritating to a wearer's skin. Generally, at least a portion of the topsheet 124 is liquid pervious, permitting liquid to readily penetrate through the thickness of the topsheet 124. One topsheet 24 useful herein is available from BBA Fiberweb, Brentwood, Tenn. as supplier code 055SLPV09U. The topsheet 124 may be apertured.

Any portion of the topsheet 124 may be coated with a lotion or skin care composition as is known in the art. Non-limiting examples of suitable lotions include those described in U.S. Pat. Nos. 5,607,760; 5,609,587; 5,635,191; and 5,643,588. The specific examples are not limiting, as any lotion or skin care composition known in the art may be utilized. The topsheet 124 may be fully or partially elasticized or may be foreshortened so as to provide a void space between the topsheet 124 and the core 128. Exemplary structures including elasticized or foreshortened topsheets are described in more detail in U.S. Pat. Nos. 4,892,536; 4,990,147; 5,037,416; and 5,269,775.

Figure 6:
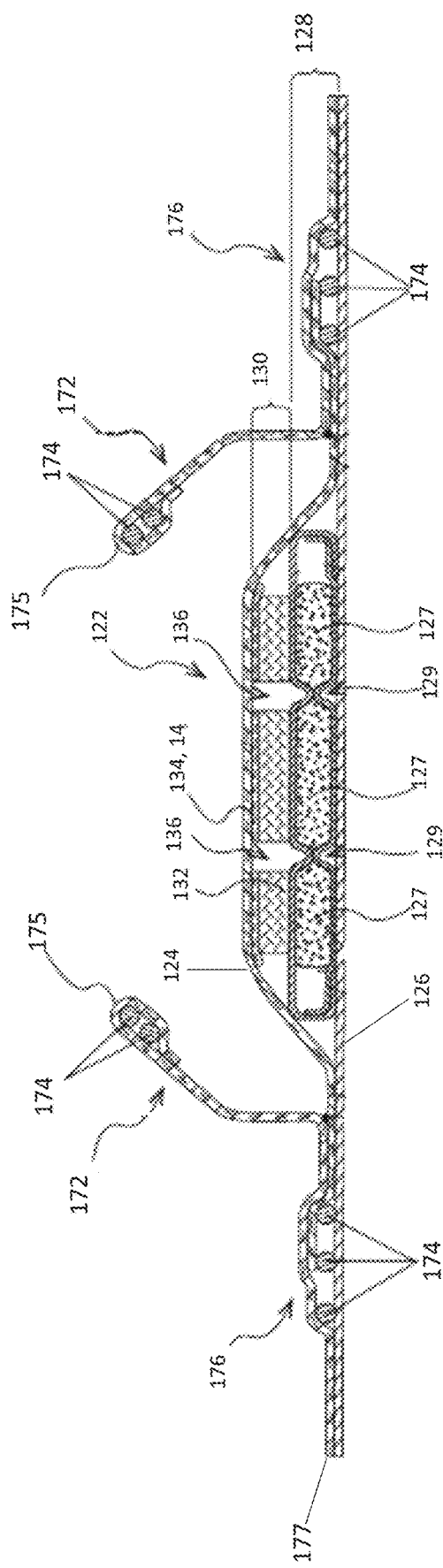
FIG. 6 is a cross-sectional view of the absorbent article taken about the lateral centerline in FIG. 4 in accordance with a non-limiting embodiment of the present invention.

Absorbent Core:

As shown in FIG. 6, the absorbent core 128 may comprise a wide variety of liquid-absorbent materials 127 commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. The absorbent material 127 may be at least partially surrounded by a core wrap.

In some embodiments, the core may comprise one or more channels 129, which are substantially free of absorbent material. In one nonlimiting example, one or more channels may extend longitudinally.

Nonlimiting exemplary absorbent structures for use as the absorbent core 128 are described in U.S. Pat. Nos. 4,610,678; 5,260,345; 5,387,207; 5,397,316; 5,625,222; 8,979,815, 9,060,904, and 9,072,634; and U.S. patent application Ser. No. 13/491,642.

Backsheet:

The backsheet 126 is generally positioned such that it may be at least a portion of the garment-facing surface of the absorbent article 100. Backsheet 126 may be designed to prevent the exudates absorbed by and contained within the absorbent article 20 from soiling articles that may contact the absorbent article 20, such as bed sheets and undergarments. The backsheet 126 is impervious to liquids. Suitable backsheet 126 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 100 while still preventing exudates from passing through the backsheet 126. Exemplary breathable materials may include materials such as woven webs, nonwoven webs, polymeric films such as thermoplastic films of polyethylene or polypropylene, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 126 including, but not limited to, surface treatments, particular film selections and processing, particular filament selections and processing, etc. In one nonlimiting example, the backsheet is a thermoplastic film having a thickness of from about 0.012 mm to about 0.051 mm.

Backsheet 126 may also consist of more than one layer. The backsheet 126 may comprise an outer cover and an inner layer. The outer cover may be made of a non-woven material 14. The inner layer may be made of a substantially liquid-impermeable film, such as a polymeric film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR.

Figure 5:
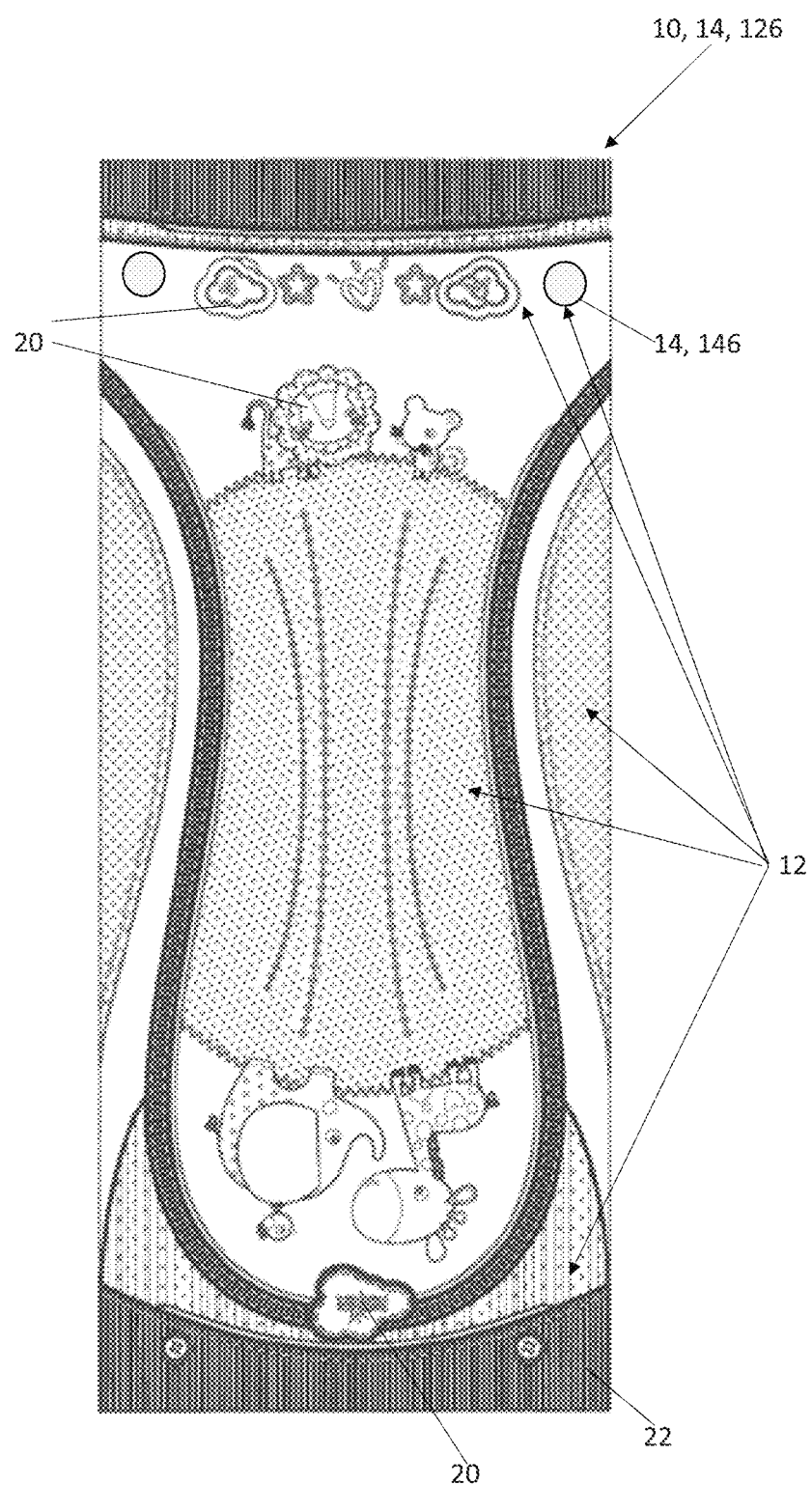
FIG. 5 is a schematic, plan view of a backsheet in accordance with one nonlimiting embodiment of the present invention.

In some embodiments, the backsheet 126 comprises one or more printed portions 12 as is shown in FIG. 5. The printed portions 12 (on the backsheet or elsewhere) may comprise energy curable inks 24, which may be disposed in one or more patterns 22 and/or design elements 20 including but not limited to graphics, instructional indicia, and insignia.

While a variety of backsheet configurations are contemplated herein, it would be obvious to those skilled in the art that various other changes and modifications can be made without departing from the spirit and scope of the invention.

Acquisition-Distribution System (ADS)

Turning to FIG. 6, the absorbent article may comprise an ADS 130. One function of the ADS is to quickly acquire one or more of the fluids and distribute them to the absorbent core in an efficient manner. The ADS may comprise one, two or more layers, which may form a unitary layer or may remain as discrete layers which may be attached to each other. In certain embodiments, the ADS may be substantially free (e.g., 80%, 85%, 90%, 95%, or 99% free of) or completely free of SAP. In nonlimiting examples, the ADS may comprise a distribution layer 132 and/or an acquisition layer 134. In various embodiments, the acquisition layer 134 may acquire bodily exudates and the distribution layer 132 may distribute bodily exudates or both layers may distribute and/or acquire bodily exudates. An ADS disclosed herein may be positioned in an absorbent article: (1) intermediate a liquid pervious material or topsheet and an absorbent core; (2) intermediate an absorbent core and a liquid impervious material or backsheet; or may be otherwise located within the absorbent article. In an embodiment, more than one ADS may be provided in an absorbent article.

In a certain embodiment, the ADS may comprise chemically cross-linked cellulosic fibers. In nonlimiting examples, the distribution layer 132 may comprise at least 50%, or 60%, or 70%, or 80%, or 90%, or even up to 100%, by weight of the layer, of cross-linked cellulose fibers (including the cross-linking agents). The cross-linked cellulosic fibers may be crimped, twisted, or curled, or a combination thereof including crimped, twisted, and curled. Example chemically cross-linked cellulosic fibers are disclosed in U.S. Pat. No. 5,137,537. In certain embodiments, the chemically cross-linked cellulosic fibers are cross-linked with between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent based on glucose unit. Citric acid is an example cross-linking agent. In other embodiments, polyacrylic acids may be used. Further, according to certain embodiments, the cross-linked cellulosic fibers have a water retention value of about 25 to about 60, or about 28 to about 50, or about 30 to about 45. A method for determining water retention value is disclosed in U.S. Pat. No. 5,137,537. Example chemically cross-linked cellulosic fibers suitable for a distribution layer are disclosed in U.S. Pat. Nos. 5,549,791, 5,137,537, WO 9534329, or U.S. Pat. App. Publ. No. 2007/118087, U.S. Pat. Publ. No. 2008/0312622 A1.

The distribution layer may typically have an average basis weight of from 30 to 400 g/m$^2$ or from 100 to 300 g/m$^2$, specifically reciting all 1.0 g/m$^2$ increments within the above-specified ranges and any ranges formed therein or thereby. The density of the distribution layer may vary depending on the compression of the absorbent article, but may be between 0.03 to 0.15 g/cm$^3$ or 0.08 to 0.10 g/cm3, specifically reciting all 1.0 g/cm3 increments within the above-specified ranges and any ranges formed therein or thereby, measured at 0.30 psi (2.07 kPa).

Additionally or alternatively, the ADS 130 may comprise an acquisition layer 134. In an embodiment, the acquisition layer 134 may be disposed, for example, between the distribution layer 132 and the topsheet 124. The acquisition layer 134 may comprise a nonwoven 14, such as an SMS or SMMS material, comprising a spunbond, a melt-blown and a further spunbond layer or alternatively a carded chemical-bonded nonwoven. In some embodiments, the acquisition layer 134 may comprise air or wet-laid cellulosic, cross-linked cellulosic, or synthetic fibers, or blends thereof. In certain embodiments, the acquisition layer 134 may comprise a roll-stock web of synthetic fibers (which may be processed to increase void space, such as by solid state formation), or a combination of synthetic and cellulosic fibers, bonded together to form a high loft material. Alternatively, the acquisition layer 134 may comprise absorbent open cell foam. The nonwoven material may be latex bonded. Example acquisition layers are disclosed in U.S. Pat. No. 7,786,341. Carded, resin-bonded nonwovens may be used, in particular where the fibers used are solid round or round hollow PET staple fibers (50/50 or 40/60 mix of 6 denier and 9 denier fibers). The acquisition layer 134 may be stabilized by a latex binder, for example a styrene-butadiene latex binder (SB latex).

A further acquisition layer may be used in addition to a first acquisition layer described above. For example, a tissue, nonwoven, or other layer may be placed between the first acquisition layer and the distribution layer. The tissue may have enhanced capillarity distribution properties compared to the acquisition layer described above. The tissue, nonwoven, or other layer and the first acquisition layer may be of the same size or may be of a different size. For example, the tissue, nonwoven, or other layer may extend further in the rear of the absorbent article than the first acquisition layer. An example of hydrophilic tissue is a 13-15 gsm high wet strength made of cellulose fibers from supplier Havix.

In some embodiments, one or more layers of the ADS may comprise channels 136. One or more of the channels 136 may be configured to work in concert with one or more channels 129 in the absorbent core 128, as discussed above. Furthermore, channels 136 may also provide increased void space to hold and distribute urine, feces or other body exudates within the absorbent article, leading to reduced leakage and skin contact.

In some embodiments, the ADS 130 comprises one or more printed portions 12. The printed portions 12 may comprise energy curable inks 24, which may be disposed in one or more patterns 22 and/or design elements 20 including but not limited to graphics, instructional indicia, and insignia. In some nonlimiting examples, the printed portion 12 is disposed on the acquisition layer 134.

Suitable ADS are described in WO 2000/59430, WO 95/10996, U.S. Pat. No. 5,700,254, WO 02/067809, and US Pat. Pub. No. 2015/065973 for example.

Ears/Fasteners:

The absorbent article 100 may include front ears and/or back ears 140 as shown in FIG. 4. The ears may be an integral part of the chassis, such as formed from the topsheet 124 and/or backsheet 126 as side panels. Alternatively, the ears may be separate elements attached by gluing, heat embossing, and/or pressure bonding. Each ear may be extensible or inextensible. The ears 140 may be formed from nonwoven webs, woven webs, knitted fabrics, polymeric and elastomeric films, apertured films, sponges, foams, scrims, and combinations and laminates thereof. In some embodiments, the ear may include elastomers (e.g., elastic strands, LYCRA® fibers), such that the ear is stretchable. In further embodiments, an ear 140 may comprise a printed portion 12 having an energy curable ink 24 which may be disposed in one or more patterns 22 and/or design elements 20 including but not limited to graphics, instructional indicia, and insignia as illustrated in FIG. 4.

The absorbent article 100 may also include a fastening system 142. When fastened, the fastening system 142 interconnects the first waist region 116 and the rear waist region 118 resulting in a waist circumference that may encircle the wearer during wear of the absorbent article 10. The fastening system 142 may comprise a fastener 144 such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 142 may also provide a means for holding the article in a disposal configuration as disclosed in U.S. Pat. No. 4,963,140. The fastening system 142 may also include primary and secondary fastening systems, as disclosed in U.S. Pat. No. 4,699,622. The fastening system 142 may be constructed to reduce shifting of overlapped portions or to improve fit as disclosed in U.S. Pat. Nos. 5,242,436; 5,499,978; 5,507,736; and 5,591,152. In some embodiments, the fastening system 142 and/or the fastener 144 is foldable.

Stretchable ears and/or fastening members may facilitate the attachment of the fastening members to a landing zone 146 and/or maintain the taped diapers in place around the wearer's waist. The landing zone 146 may be a portion of the backsheet 126, or may be a separate substrate 10, such as a nonwoven substrate 14, joined to the backsheet. In some embodiments, the landing zone 146 comprises a printed portion 12 as is depicted in FIG. 5. The printed portion 12 may comprise an energy curable ink, which may be disposed in one or more patterns 22 and/or design elements 20 including but not limited to graphics, instructional indicia, and insignia.

Extensible ears and/or fastening members may provide a more comfortable and contouring fit by initially conformably fitting the absorbent article to the wearer and sustaining this fit throughout the time of wear well past when absorbent article has been loaded with fluids or other bodily exudates since the elasticized ears allow the sides of the absorbent article to expand and contract. Exemplary ears and/or fastening systems are disclosed in U.S. Pat. Nos. 6,863,666; 6,132,411; 7,870,652; 8,992,499; 8,690,852; 8,382,736.

Leg Gasketing System

As illustrated in FIG. 4 and FIG. 6, the absorbent article 100 may comprise a leg gasketing system 170 attached to the chassis 122, which may comprise one or more cuffs. The leg gasketing system may comprise a pair of barrier leg cuffs 172. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximal edge joined directly or indirectly to the topsheet 124 and/or the backsheet 126 and a free terminal edge 175, which is intended to contact and form a seal with the wearer's skin. In some embodiments, the free terminal edge 175 comprises a folded edge. The barrier leg cuffs 172 extend at least partially between the front waist edge 113 and the rear waist edge 114 of the absorbent article on opposite sides of the longitudinal axis 110 and are at least present in the crotch region. The barrier leg cuffs may be joined at the proximal edge with the chassis of the article by a bond which may be made by gluing, fusion bonding, or a combination of other suitable bonding processes.

The barrier leg cuffs may be integral with the topsheet 124 or the backsheet 126 or may be a separate material joined to the article's chassis. Each barrier leg cuff 172 may comprise one, two or more elastic elements 174 close to the free terminal edge 175 to provide a better seal. Additionally or alternatively, one or both of the barrier cuffs 172 may comprise a nonwoven 14. In some embodiments, a barrier leg cuff 172 comprises a printed portion 12. The printed portion 12 may comprise an energy curable ink 24, which may be disposed in one or more patterns 22 and/or design elements 20 including but not limited to graphics, instructional indicia, and insignia.

In addition to the barrier leg cuffs 172, the article may comprise gasketing cuffs 176, which are joined to the chassis of the absorbent article, in particular to the topsheet 124 and/or the backsheet 126 and are placed externally relative to the barrier leg cuffs 172. The gasketing cuffs 176 may provide a better seal around the thighs of the wearer. A gasketing cuff may comprise a proximal edge and a free terminal edge 177. The free terminal edge 177 may comprise a folded edge. Each gasketing cuff may comprise one or more elastic elements 174 in the chassis of the absorbent article between the topsheet 124 and backsheet 126 in the area of the leg openings. Additionally or alternatively, one or both of the gasketing cuffs 176 may comprise a nonwoven 14. In some embodiments, a gasketing leg cuff 176 comprises a printed portion 12 as shown in FIG. 4. The printed portion 12 may comprise an energy curable ink 24, which may be disposed in one or more patterns 22 and/or design elements 20 including but not limited to graphics, instructional indicia, and insignia.

All, or a portion of, the barrier leg cuffs and/or gasketing cuffs may be treated with a lotion or another skin care composition. In further embodiments, the leg gasketing system comprises barrier leg cuffs that are integral with gasketing cuffs.

Suitable leg gasketing systems which may be part of the absorbent article are disclosed in U.S. Pat. App. No. 62/134,622, Ser. No. 14/077,708; U.S. Pat. Nos. 8,939,957; 3,860,003; 7,435,243; 8,062,279.

Waist Feature

The absorbent article 100 may comprise at least one elastic waist feature 180 that helps to provide improved fit and containment, as shown in FIG. 4. The elastic waist feature 180 is generally intended to expand and contract to dynamically fit the wearer's waist. Elasticized waist features 180 include waistbands, waist cuffs having pockets formed from a portion of the waist feature 180 that is unattached from the chassis 122, and waist panels designed to fit securely about the abdomen of the wearer. Nonlimiting examples of elasticized waist features are disclosed in U.S. patent application Ser. Nos. 13/490,543; 14/533,472; and 62/134,622. Waist features 180 may be joined to the chassis 122 in the first waist region 116 and/or in the second waist region 118. In some embodiments, a waist feature 180 comprises a nonwoven substrate 14. In further embodiments, the waist feature 180 comprises a printed portion 12 (not shown). The printed portion 12 may comprise an energy curable ink 24, which may be disposed in one or more patterns 22 and/or design elements 20 including but not limited to graphics, instructional indicia, and insignia. In some embodiment, the waist feature 180 comprises a belt 220 which is discussed in more detail below.

Adult or Baby Pant Absorbent Articles

In some embodiments, the article 100 may comprise an absorbent pant 200 as shown in FIGS. 7a-7b. The absorbent pant may comprise include a chassis 122, a belt 220 to be positioned about the wearer's waist, and optionally a leg gasketing system 170. FIG. 7b depicts an exemplary precursor structure of the pant in FIG. 7a, in an open configuration laid out flat and stretched out laterally against elastic-induced contraction. In the final assembly of the pant, the front belt portion 222 is joined to rear belt portion 223 at seams 224, which may be permanent or refastenable. To form the pant 200, the precursor structure may be folded at or about lateral centerline 120 with the topsheet 124 facing inward, and the longitudinal edges of the front 222 and rear 223 belt portions may be joined at seams 224, forming a pant structure having leg openings, front waist edge and rear waist edge. In this way, the pant 12 may comprise a pre-formed, continuous waist opening and pre-formed, continuous leg openings for the wearer at the time of donning the pant 200.

The front and rear belt portions 222, 223 may be the outermost structures forming the front and rear regions of a pant 200. The pant may include an outer wrap 226 wrapping the entirety of the front, crotch and rear regions, and forming an outermost pant-shaped structure. In some embodiments, the outer cover of the backsheet forms the outer wrap. Additional layer(s) and elastic members 228 to form front and rear belt portions 222, 223 may be disposed to the inside of outer wrap 226, and be suitably affixed thereto by adhesive lamination, bonding or any other suitable mechanism. An outer wrap 226 may be formed of one or more sections of nonwoven web and may be cut to a profile providing suitably tailored leg opening edge profiles as desired.

Any waist feature 180, including one or both of front and rear belt portions 222, 223 may be formed of layers of nonwoven substrate 14, which respectively form inner and outer layers. Suitable nonwoven substrates 14 that may be useful in the present invention also include, but are not limited to spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers, as known in the art. The nonwoven web may be formed predominately of polymeric fibers. In some examples, suitable non-woven fiber materials may include, but are not limited to polymeric materials such as polyolefins, polyesters, polyamide, or specifically, polypropylene (PP), polyethylene (PE), poly-lactic acid (PLA), polyethylene terephthalate (PET) and/or blends thereof. In some examples, the fibers may be formed of PP/PE blends such as described in U.S. Pat. No. 5,266,392. Nonwoven fibers may be formed of, or may include as additives or modifiers, components such as aliphatic polyesters, thermoplastic polysaccharides, or other biopolymers. Further useful nonwovens, fiber compositions, formations of fibers and nonwovens and related methods are described in U.S. Pat. Nos. 6,645,569; 6,863,933; and 7,112,621; and in U.S. patent application Ser. Nos. 10/338,603; 10/338,610; and Ser. No. 13/005,237. The individual fibers of a nonwoven layer may be monocomponent or multicomponent (including bicomponent). The multicomponent fibers may be bicomponent, with differing polymeric components in, e.g., a core-and-sheath or side-by-side arrangement. The individual components may include polyolefins such as polypropylene or polyethylene, or their copolymers, or polyesters, thermoplastic polysaccharides or other biopolymers.

According to some nonlimiting examples, the nonwoven used for a belt portion may include a material that provides good recovery when external pressure is applied and removed. Further the nonwoven may include a blend of different fibers selected, for example from the types of polymeric fibers described above. In some examples, at least a portion of the fibers may exhibit a spiral curl which has a helical shape. According to one example, the fibers may include bicomponent fibers, which are individual fibers each including different materials, usually a first and a second polymeric material. It is believed that the use of side-by-side bi-component fibers is beneficial for imparting a spiral curl to the fibers. Examples of potentially suitable curled or "crimped" bicomponent fibers and nonwovens formed from them are described in U.S. Pat. Nos. 5,382,400; 5,418,045; 5,707,468; 6,454,989; 6,632,386; 5,622,772 and 7,291,239. For purposes herein, use of a nonwoven formed of crimped bicomponent or multicomponent fibers such as, for example, described in the patents and/or patent applications cited immediately above, may be desired as one or both layers 320, 322 used to form the belt portions, because they can feel particularly soft to the touch (for wearer comfort on the inside and aesthetically pleasing feel on the outside) and are generally quite pliable.

Waist features, such as belt portions, may further comprise one or more elastic members 228. The elastic members 228 may be elastomeric fibers, such as LYCRA® fibers available from INVISTA of Wichita, Kans., in various decitex levels. The elastic members 228 may also comprise any heat shrinkable elastic material as is well known in the art. Other suitable elastics can be made various other materials including but not limited to: rubbers, styrene ethylbutylene styrene, styrene ethylene propylene styrene, styrene ethylene propylene styrene, styrene butadiene styrene, styrene isoprene styrene, polyolefin elastomers, elastomeric polyurethanes, and other elastomeric materials known in the art, and combinations thereof. In some nonlimiting examples, the elastic members may be extruded strand elastics with any number of strands (or filaments). In some embodiments, the elastic members can have a decitex ranging from 50 to 2000, or any integer value for any decitex value in this range. However, the skilled person may select the appropriate decitex based on the desired contraction and other principles discussed herein. In further embodiments, the elastic members may be in a form of film. Examples of films have been described in prior patent applications (see, for example, U.S. Pat. App. Pub. No. 2010/0040826). The film may be created with a variety of resins combined in at least one of several sublayers, the latter providing different benefits to the film.

In addition, elastic members 228 may take a multitude of configurations. For example, the width may be varied; a single strand or several parallel or non-parallel strands of elastic material may be used; or a variety of shapes may be used including rectilinear and curvilinear; or a variety of cross sectional shapes can be used (circular, rectangular, square, etc.).

Layers of a waist feature (e.g., belt portion) and/or chassis 122 may be joined together about elastic strands 228 by adhesive deposited between the layers, by thermal bonds, by compression bonds, or by a combination thereof. In other examples, the one or more elastic members may be strips or a section of film formed of elastomeric material. Where the elastic member is elongate, it may be desirable that the longer dimension be laterally oriented, or even substantially aligned with the lateral direction, as strands 228 are depicted in FIG. 7b for example.

A belt portion or other form of waist feature may comprise at least 3 waist elastic members 43, at least 5 elastic members 43, at least 10 waist elastic members 43, or at least 15 waist elastic members 228, or from about 2 to about 35 waist elastic members, or from about 5 to about 25 waist elastic members, reciting for each range every 1 increment therein.

In one embodiment, adjacent elastic members 228 are spaced a longitudinal distance of at least 3.5 mm apart from one edge of the member to the other edge of the member, optionally at least 4 mm apart; optionally at least 4.5 mm apart; optionally at least 5 mm apart; optionally at least 5.5 mm apart; optionally at least 6 mm apart; optionally at least 6.5 mm apart; optionally at least 7 mm apart; optionally at least 7.5 mm apart; optionally at least 8 mm apart; optionally at least 8.5 mm apart; optionally at least 9 mm apart; optionally at least 9.5 mm apart; optionally at least 10 mm apart; optionally at least 10.5 mm apart; optionally at least 11 mm apart; optionally at least 11.5 mm apart; optionally at least 12 mm apart. The spacing between elastic members may be the same or different across the longitudinal length of the waist feature. For example, the spacing between adjacent elastic members could uniformly be 7 mm or there could be variable spacing (i.e., two adjacent elastic members are separated by 3 mm, another two are separated by 6.5 mm, etc.).

During manufacture of the waist feature, the elastic members 228 may be pre-strained by a desired amount as they are being incorporated into the waist feature. Upon subsequent relaxation of the waist feature, the elastic members will contract laterally toward their unstrained lengths. This may cause layers of the waist feature to gather and form ruffles or rugosities having ridges and valleys generally transverse to the lengths of the elastic members 228, and extending in the z-direction.

In further embodiments, to adhere the components of the waist feature laminate, the elastic members may be individually coated with adhesive ("strand coated") prior to incorporation into the waist laminate. Various coating methods and techniques, including strand coating methods and techniques, are shown for example in U.S. Pat. Nos. 5,340,648; 5,501,756; 5,507,909; 6,077,375; 6,200,635; 6,235,137; 6,361,634; 6,561,430; 6,520,237; 6,582,518; 6,610,161; 6,613,146, 6,652,693, 6,719,846 and 6,737,102. The adhesive used may be a hot-melt type adhesive having elasticity and flexibility making it suitable for attaching pre-strained elastic materials to substrates, such as OMNIMELT BLOCKS 22 H2401F, or ZEROCREEP brands such as AVANCÉ, available from Bostik, Inc., Wauwatosa, Wis.

In certain embodiments, corners of the front and/or rear belt portion may be trimmed off as suggested in FIG. 7b. The corners may be trimmed off along straight lines, or may be trimmed off along trim paths that are curved and either concave or convex with respect to the remaining area of the belt portion (see FIG. 7b), as may be desired to impart a particular curved leg edge profile. In conjunction with such trimming and the configuration of elastic strands described above, it may be desired to impart bonding between layers along edges of the respective belt portion 222, 223. Such bonding may serve to prevent any separation of the layers along edges that may contribute to creating a ragged appearance, and may also help the rear belt portion more effectively draw inward laterally toward the central chassis 122, under the contractive force of the elastic strands below seams 224. Bonding may be effected by mechanical/compression bonds as described in, for example, U.S. Pat. Nos. 4,854,984 and 4,919,738, by thermal bonds or welds, or by deposits of adhesive between layers. In nonlimiting examples, such bonding may form a pattern along edges. Such bonding may be supplemental to any bonding between layers generally holding the respective belt portion 222, 223 together as a laminate structure.

Side seams 224 may be permanent or refastenable. Permanent seams may be formed between the front belt portion and the rear belt portion by any bonding mechanism wherein the front and rear belt portions may not be forcibly separated without substantial damage to one or both of the front and rear belt portions, or without any included mechanism by which substantial reattachment or refastening may be effected. Bonding forming permanent seams may include compression bonding, thermal bonding/welds, ultrasonic bonding or adhesive bonding. Refastenable seams may be formed between the front belt portion and the rear belt portion by any mechanism configured to permit substantially non-destructive forcible separation of the front and rear belt portions, and subsequent substantial reattachment or refastening at the same locations. One example of such mechanism is a hook-and-loop fastening system, for example, a VELCRO fastening system. A suitably sized and shaped hooks component may be bonded to one of the front or rear belt portions along the longitudinal edges thereof, and a suitably sized and shaped loops component may be bonded to the other of the front or rear belt portions along the longitudinal edges thereof, in positions in which they may be brought together and engaged to form seams 224. Examples are depicted in U.S. Pat. App. Ser. Nos. 61/787,416; 61/787,332; 61/666,065.

Exemplary belt and absorbent pant constructions are disclosed in U.S. patent application Ser. Nos. 14/598,783 and 14/032,595.

In some embodiments, the belt 220 may comprise one or more printed portions 12 having energy curable ink 24. The energy curable ink may be disposed in one or more patterns 22 and/or design elements 20 including but not limited to graphics, instructional indicia, and insignia.

Package

The absorbent articles 100 of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 8:
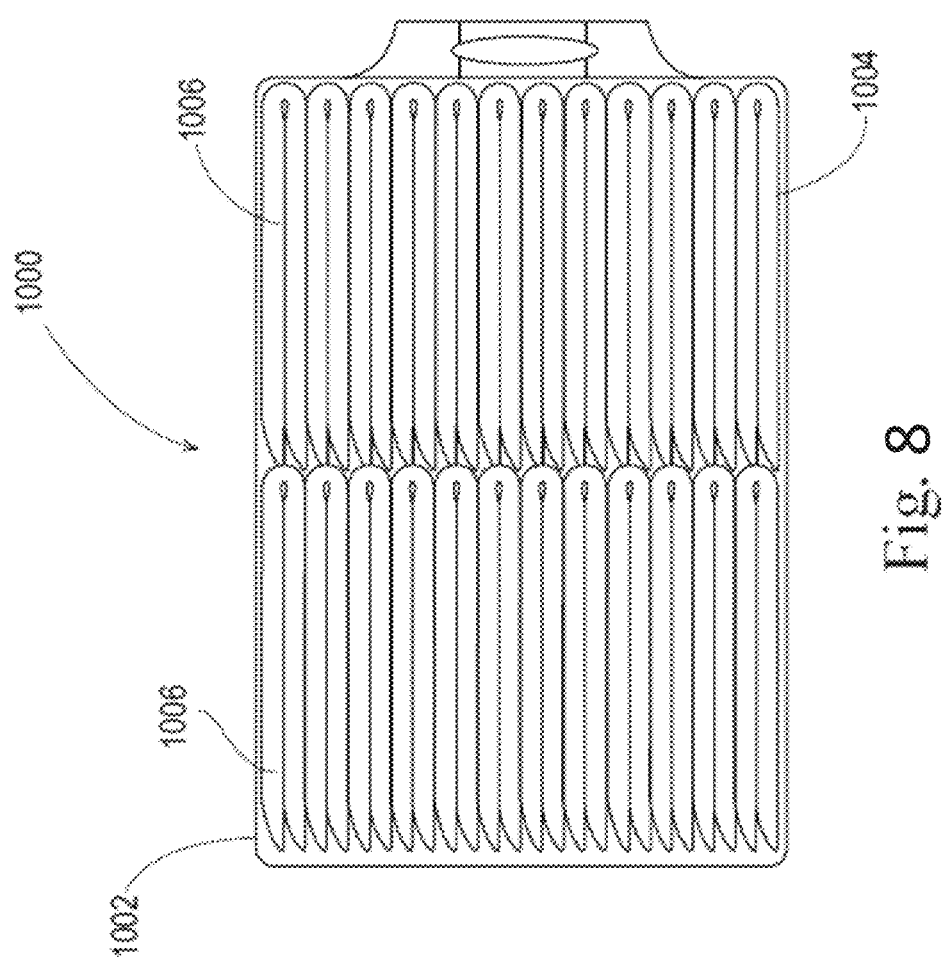
FIG. 8 is a schematic perspective view of a package in accordance with one embodiment of the present invention.

FIG. 8 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Combinations

A. A nonwoven substrate comprising a first surface and a second surface opposite the first surface; wherein the first surface comprises one or more printed portions, wherein at least one printed portion comprises a curable ink; and wherein the at least one printed portion comprises a Crosslinking Index of about 330 or less, or in particular 200 or less, or more specifically 100 or less as determined by the Crosslinking Index Test Method herein.

B. A nonwoven substrate according to paragraph A wherein the at least one printed portion further comprises an IAR (Mineral Oil) of 1.30 or greater, or more specifically 2.5 or greater, or from about 0.5 to about 5 as determined by the IAR Test Method herein.

C. A nonwoven substrate according to any of the preceding paragraphs wherein the at least one printed portion further comprises an Ink Penetration Depth of about 250 microns or less according to the Ink Penetration Depth Test Method herein.

D. A nonwoven substrate according to any of the preceding paragraphs wherein the at least one printed portion comprises a ΔE* of about 7 or greater, or more specifically from about 12 to about 50, or about 10 or greater as determined by the ΔE* Determination Test Method herein.
E. A nonwoven substrate according to any of the preceding paragraphs wherein the at least one printed portion comprises an IAR (Dry) of about 1.0 or greater, or 1.5 or greater, or about 3.5 or greater, or from about 3.5 to about 4.5 as determined by the IAR Test Method herein.
F. A nonwoven substrate according to any of the preceding paragraphs wherein the at least one printed portion comprises an IAR(Synthetic Urine) of about 2 or greater, or about 3 or greater, or from about 2 to about 5 as determined by the IAR Test Method herein.
G. A nonwoven substrate according to any of the preceding paragraphs further comprising a basis weight of about 8 gsm to about 65 gsm.
H. A nonwoven substrate according to any of the preceding paragraphs further comprising polyolefin fibers.
I. A nonwoven substrate according to any of the preceding paragraphs wherein the curable ink comprises an e-beam curable ink.
J. A nonwoven substrate according to any of the preceding paragraphs wherein the curable ink comprises a UV curable ink, optionally a LED UV curable ink.
K. A nonwoven substrate according to any of the preceding paragraphs wherein the curable ink is at least partially disposed in a graphic and/or pattern.
L. A nonwoven substrate according to any of the preceding paragraphs wherein the curable ink comprises any of the colors of cyan, magenta, yellow, black and combinations thereof.
M. An article comprising a topsheet, backsheet and absorbent core disposed between the topsheet and backsheet and a component comprising a nonwoven substrate according to any of the preceding paragraphs.
N. The article according to paragraph M wherein the component is selected from the backsheet, the topsheet, an acquisition distribution system disposed between the topsheet and the absorbent core, a leg cuff joined to the chassis, an ear joined to the chassis, a belt joined to the chassis and combinations thereof.
O. A package comprising a plurality of the absorbent articles according to paragraphs M or N.
P. The package of paragraph O wherein the package exhibits an In-Bag Stack Height of from about 70 mm to about 110 mm.

Test Methods
Crosslinking Index Method

Crosslinking Index in printed ink are measured using Attenuated Total Reflection (ATR) FTIR based on their unreacted C=C functional groups. Spectra are collected using an FTIR equipped with a micro-ATR, diamond, single bounce crystal attachment (a suitable system is a Bruker Vertex 80 FTIR, or equivalent and a Smiths Detection Durascope Micro-ATR, or equivalent). Measurements are made at a printed site and an adjacent non-printed site to obtain the Crosslinking Index. Five measurements are performed on a total of three products.

The instrument is calibrated and operated as per the instructions of the manufacturer. The FTIR is programed to perform 64 scans at a resolution of 4.0 $cm^{-1}$ from 550 to 4000 $cm^{-1}$ for each measurement. Background scans of a clean ATR crystal are performed before every measurement and used for background correction.

Remove the printed substrate of interest from the sample. Determine the side on which the printed ink was applied and make all measures on that side. Select a non-bonded, inked site on the substrate for measurement. Focus the micro-ATR on a region that has full ink coverage and collect an "inked" scan. Select an adjacent site on the substrate that is not printed, focus the micro-ATR on a region that has no ink coverage and collect a non-inked scan. In like fashion, make five (5) different paired measurements at different printed locations on the specimen.

For each scan, appropriate software is used to measure peak heights from the absorbance versus wavenumber plot. For the scan from the inked area, draw a linear, point to point baseline between 770 $cm^{-1}$ and 880 $cm^{-1}$. Measure the vertical drop from the highest peak between 830 $cm^{-1}$ and 850 $cm^{-1}$ to the baseline and record as the "Peak Height at 840". Measure the vertical drop from the highest peak between 800 $cm^{-1}$ and 820 $cm^{-1}$ to the baseline and record as the "Peak Height at 810". Calculate and record the 810/840 Peak Ratio for the inked area as the Peak Height at 810 divided by the Peak Height at 840. In like fashion, repeat for the scan from the non-inked area to calculate the 810/840 Peak Ratio for the non-inked area. Crosslinking Index is calculated using the following equation:

$$\text{Crosslinking Index} = \frac{\left(\frac{810}{840}\text{Peak Ratio}\right)_{Inked} - \left(\frac{810}{840}\text{Peak Ratio}\right)_{non\text{-}inked}}{\left(\frac{810}{840}\text{Peak Ratio}\right)_{non\text{-}inked}} \times 100$$

Calculate the Crosslinking Index for each of the 5 locations on the specimen. In like fashion, analyze a total of three (3) different samples selecting equivalent locations on each sample. Calculate and report the arithmetic mean for the fifteen Crosslinking Index values to the nearest 0.1%.

ΔE* Determination Method

ΔE* Determination analysis is made using a 45° circumferential illumination/0° viewing spectrophotometer capable of making standard CIE L*a*b* measurements in accordance with ASTM E1349. The instrument is configured with a port diameter of 4.0 mm or other diameter appropriate for the size of the region to be measured, such that only the printed region is observed within the port. Set the instrument parameters to 2° Observer, Illumination C, Density Measurement Condition M0 (no filter, UV included), Absolute Density White Balance, and ISO (ANSI) Reflectance Status T. A White Standard Board, available as PG2000 from Sun Chemical-Vivitek Division, Charlotte, N.C. or equivalent, is used as a specimen backing. Analysis is performed in a room controlled at about 23° C.±2 C.° and 50%±2% relative humidity. Samples and the White Standard Board are conditioned at the same condition for 2 hours before testing. Calibrate the instrument per the vender's instructions.

Remove the printed substrate of interest from the article. Determine the side on which the printed ink was applied and make all measures on that surface. Select the printed site to be measured. Place the specimen, printed side facing upward onto the Standard White Board. Align the measurement port of the instrument on the specimen, ensuring only the printed region of interest is visible within the port. Take a reading of L*a*b* and record the value to the nearest 0.01 units. Next take a color measurement on a non-printed region of the substrate and record the L*a*b* values to the nearest 0.01 units. Calculate the difference ΔE* between the printed and non-printed sites as:

$$\Delta E^* = [(L^*_{print} - L^*_{no-print})^2 + (a^*_{print} - a^*_{no-print})^2 + (b^*_{print} - b^*_{no-print})^2]^{0.5}$$

In like fashion make three ΔE* Determination measurements on equivalent sites on three replicate samples. Calculate the arithmetic mean of ΔE* for the replicates and report each to the nearest 0.01 units.

Ink Basis Weight Test Method

Place an absorbent material in a pan for collecting the ink from the printheads.

Place the pan and absorbent material on a scale and zero the scale.

Place the pan under a single row of printheads. Try to get the absorbent material as close to the printheads as possible without letting the absorbent material touch the printheads.

Create a single color image with a rectangle of known length, width, and % fill.

Set the printer to the desired firing frequency based upon the desired MD resolution and MD substrate speed.

Firing Frequency=MD Resolution×MD Substrate Speed

Tell the printer to fire 500 repeats of the single color rectangle.

Fire the printer so the ink is captured in the pan with the absorbent material.

Remove the pan and absorbent material from under the printheads, and place the pan on the scale that was zeroed earlier.

Note the mass (g) displayed on the scale. This is the mass of the ink that was ejected from the printer when it was printing 500 repeats of the single color rectangle.

The equation for calculating ink basis weight (g/m²):

$$\text{Ink Basis Weight (gsm)} = \frac{\text{Mass of ink (g)}}{\text{\# of repeats} \times \text{image length (m)} \times \text{image width (m)}}$$

For Example
MD Resolution: 100 dpi (dots per inch)
MD Substrate Speed: 20 inches per second Firing Frequency=100×20=2000 Hz Image Length: 0.1 m
Image Width: 0.1 m
Mass of Ink: 25 grams $$\text{Ink Basis Weight (gsm)} = \frac{25}{500 \times 0.1 \times 0.1} = 5 \text{ gsm}$$

Ink Adhesion Rating Test Method

Ink Adhesion Rating measures the amount of color transferred from the surface of a printed substrate to the surface of a standard woven receptor swatch by rubbing using a Gakushin-type Rubbing Tester (a suitable instrument is a Model RT-300, available from Daiei Kagaku Seiki, Kyoto Japan, or equivalent). The instrument uses the 2N (200 g) Friction Head, with no supplemental weights, and executes a stroke length of 120 mm at 30 rpm. A "dry" test is performed with an unmodified receptor swatch, while the "wet" test is performed with a receptor swatch that has been dosed with a specified amount of mineral oil. The ink transfer is quantified using a 0° illumination/45° circumferential viewing spectrophotometer suitable for making standard CIE L*a*b* color measurements in accordance with ASTM E1349 (a suitable instrument is a Hunterlab Labscan XE spectrophotometer, Hunter Associates Laboratory Inc., Reston Va., or equivalent). An Ink Adhesion Rating (IAR) that ranges from 0 to 5, wherein 0 is extensive transfer and 5 is no transfer of color, is then calculated and reported. All testing is performed at about 23° C.±2 C.° and a relative humidity of about 50%±2%.

The Receptor Swatch is a 3 inch by 1 inch woven crock-swatch, available as Shirting #3 from Testfabrics Inc., West Pittston, Pa., or equivalent. Two test fluids are used for the wet adhesion testing, mineral oil and synurine. The mineral oil used for the wet test has a boiling point of 215° C.-643° C., flash point of 115° C. to 268° C., density of 0.82 to 0.90 g/cm³, and dynamic viscosity of 0.038 Pa s at 38° C. A suitable mineral oil is available as RC-118 from G-Biosciences, St. Louis, Mo., or equivalent. The synurine is prepared by dissolving 10.00 g Potassium Chloride (KCl), 10.00 g Sodium Sulfate ($Na_2SO_4$), 4.25 g Ammonium Phosphate Monobasic ($NH_4H_2PO_4$), 0.75 grams Ammonium Phosphate Dibasic (($NH_4)_2HPO_4$), 1.25 grams Calcium Chloride Dihydrate ($CaCl_2.2H_2O$), and 2.50 Magnesium Chloride Hexahydrate ($MgCl_2.6H_2O$) into 5.00 Liters of purified water (e.g. water from a Milli-Q water purification system, available from Millipore, Billerica, or equivalent). The salts are >95% pure and available as Baker Analyzed reagents or equivalent.

All samples and receptor swatches are equilibrated at 230° C.±20 C and 50%±2% relative humidity for at least 2 hours before analysis. Remove the printed substrate of interest from the article. Determine the side on which the printed ink was applied and make all measures on that surface. Select the printed site to be measured and cut a specimen 9 inch×1 inch from the substrate. Prepare a total of nine (9) specimens from equivalent sites on nine replicate samples for analysis. Three of the specimens are used for the dry test, three for the wet test (mineral oil), and three for the wet test (synurine).

For the dry test, mount the three test specimens onto the movable, curved test stage with the printed sides facing away from the stage. The test specimens must be secured using spring loaded binders at both ends so that they do not move during testing. Mount the receptor swatches on the three corresponding rubbing heads via their spring clamps. At this time set aside one receptor swatch for use as a reference swatch for evaluation. Place rubbing heads with receptor swatches on the test specimens and ensure the heads are properly seated. Program the rubbing tester to perform 15 cycles. Upon completion, remove the receptor swatches from the head for evaluation.

The rubbing is repeated for the wet (mineral oil) testing in like fashion to the dry testing, except that after the specimen and receptor swatches have been secured, 0.25 mL of the mineral oil is accurately pipetted onto the surface of the receptor swatches and allowed to soak in for 1 minute before the swatch is placed onto the test specimen. At this time also pipet 0.25 mL of mineral oil onto another receptor swatch for use as the reference swatch for evaluation. Program the rubbing tester to perform 15 cycles. Upon completion, remove the receptor cloth from the head for evaluation. Wet (mineral oil) specimens can be evaluated immediately upon completion. The surfaces of the test stages and rubbing heads are cleaned thoroughly with isopropanol after the wet testing.

The rubbing is repeated for the wet (synurine) testing in like fashion to the dry testing, except in that after the specimen and receptor swatches have been secured 0.25 mL of the test fluid is accurately pipetted onto the surface of the receptor swatch and allowed to soak in for 1 minute before the swatch is placed onto the test specimen. At this time also pipet 0.25 mL of synurine onto another receptor swatch for use as the reference swatch for evaluation. Program the rubbing tester to perform 15 cycles. Upon completion, remove the receptor cloth from the head for evaluation. The wet (synurine) specimens are allowed to dry at room temperature before evaluation. The surfaces of the test stages and rubbing heads are cleaned thoroughly with isopropanol after the wet testing.

The spectrophotometer is configured with a port diameter size of 0.70 in. and a viewing area diameter of 0.5 in. Instrument parameters are set to the CIE L*a*b* color scale, D65 illumination, 10° standard observer, and nominal UV filter. Color is reported as L*a*b* values to the nearest 0.01 units. Calibrate the instrument per instructions using the standard black and white plates provided by the vendor.

The triplicate specimens from the Dry test, Wet (mineral oil) test and Wet (synurine) test are evaluated and calculated verses their respective reference swatch in the following manner. Place the center of reference receptor cloth facing the port of the color meter. Cover it with the standard white plate and make an L*a*b* measurement. Record as the background reference value to the nearest 0.01 units. In like fashion measure the test side of each of the rubbed receptor swatches and record the L*a*b* values to the nearest 0.01 units. The port and plate should be cleaned after each measurement of the wet swatches to prevent contamination between specimens.

Calculate $\Delta E^*$ for each specimen versus its reference value as:

$$\Delta E^* = [(L^*_{reference} - L^*_{rubbed})^2 + (a^*_{reference} - a^*_{rubbed})^2 + (b^*_{reference} - b^*_{rubbed})^2]^{0.5}$$

Calculate the Ink Adhesion Rating (IAR) from the $\Delta E^*$ of each specimen as:

$$IAR = -0.0001(\Delta E^*)^3 + 0.0088(\Delta E^*)^2 - 0.295(\Delta E^*) + 5.00$$

Calculate and report the Dry Ink Adhesion Rating (IAR (Dry)), Wet (mineral oil) Ink Adhesion Rating ("IAR(MO)" or "IAR (Mineral Oil)"), and Wet (synurine) Ink Adhesion Rating ("IAR(SynU)" or "IAR(Synthetic Urine)") each as the arithmetic mean of the 3 replicates to ±0.1 units.

Ink Penetration Depth Test Method

Ink Penetration Depth is measured using stereomicroscope such as a Zeiss Stemi SV 11 (available from Carl Zeiss Microimaging GmbH, Göttingen, Germany), or equivalent, equipped with a digital camera capable of capturing images at least 3.0 megapixels and compatible for use with the stereomicroscope (e.g. an OptixCam Summit OCS-3.0 camera with OC View software, available from The Microscope Store, LLC, Roanoke, Va., or equivalent). Reflected illumination from a halogen light source is used to illuminate the specimen. Linear distances within the captured images are measured using image analysis software appropriate for making calibrated distance measurements (e.g., Axiovision, Carl Zeiss Microimaging GmbH, Göttingen, Germany).

Using anew Teflon coated razor blade (GEM Stainless Steel Coated, Single Edge Industrial Blades, or equivalent), a section about 2.5 cm in length was cut from the non-woven region containing the printed feature, then mounted for viewing the cross-section by carefully placing it edge down onto double sided transparent tape (e.g., Scotch Double Sided Tape 665) stuck to a standard glass microscope slide (e.g., Precleaned Gold Seal® Rite-On Microslides or equivalent). The section was mounted perpendicular to the glass slide and microscope stage with the length running parallel to the surface of the glass slide. The sample was visually checked and adjusted, if necessary, to minimize tilting to any angle. The magnification selected was 4.8× using a Zeiss 1× Plan S objective with a 0.6× C-mount camera adaptor and 0.8× zoom or equivalent.

Once the cross-section plane of the sample was brought into view and approximate focus with an optimal camera exposure time, an image was collected. Two non-overlapping images per sample were collected. Sample images were loaded into the image analysis software and each image was spatially calibrated against and ANSI certified ruler divided into millimeter increments captured in the same manner as the sample images. Spatial calibration is used to establish pixel size and allow for conversion to standard units.

The distance of ink penetration into the nonwoven is measured, beginning from the top surface over which the ink is deposited to the point perpendicular to that surface at which ink can no longer be observed. The top surface is defined as the upper most exposed region which can be physically addressed with human hand or tool and is readily visible by the human eye. Thus the top surface is taken as the local surface specific to the ink printed point of interest on the sample. Ten measurements of ink depth penetration were made on each of the two images, wherein the measurements span the image width. As such, a total of twenty measurements are obtained per sample with all recorded to the nearest micron. An average of the twenty measurements is calculated for each sample and reported along with the median and maximum value to the nearest micron.

Percent Printed Color Area

Percent Printed Color Area is used to determine the amount of printed color coverage on a component layer of an absorbent article images acquired using a flatbed scanner. The scanner is capable of scanning in reflectance mode at a resolution of 150 dpi and 24 bit color (a suitable scanner is an Epson Perfection V750 Pro from Epson America Inc., Long Beach Calif. or equivalent). The scanner is interfaced with a computer running an image analysis program (a suitable program is ImageJ v. 1.50 or equivalent, National Institute of Health, USA). The specimen images are distance calibrated against an acquired image of a ruler certified by NIST. The resulting image is then analyzed using the image analysis program to identify the boundaries of the printed color regions and calculate the percent printed color area.

Remove the printed substrate of interest from an absorbent article using cryogenic spray (such as Cyto-Freeze, Control Company, Houston Tex.) or other means as needed to separate the substrate from other components of the article and avoid any longitudinal and lateral distortion of the specimen. Five replicates of this specimen layer, obtained from five substantially similar absorbent articles, are prepared for analysis. Precondition the specimens at about 23° C.±2 C.° and about 50%±2% relative humidity for 2 hours prior to testing.

Place the ruler on the center of the scanner bed, oriented parallel to the sides of the scanner glass, and close the lid. Acquire a calibration image of the ruler in reflectance mode at a resolution of 150 dpi (approximately 5.9 pixels per mm) and 24 bit color. Save the calibration image as an uncompressed TIFF format file. Lift the lid and remove the ruler. After obtaining the calibration image, all specimens are scanned under the same conditions and measured based on the same calibration file. Next, place the specimen onto the center of the scanner bed, lying flat, with the color printed facing surface of the specimen facing the scanner's glass surface. Cover the specimen with a white background (in this test method white is defined as having L*>94, −2<a*<2, and −2<b*<2 based on the standard CIE L*a*b* color space) and close the lid. Acquire and save a scanned image of the specimen layer. If the size of the specimen layer exceeds the available scanning area, obtain multiple scans covering the entire specimen layer and digitally stitch them together into a single image for analysis. Scan the remaining four replicates in like fashion.

Open the calibration image file in the image analysis program and perform a linear distance calibration using the imaged ruler. This distance calibration scale will be applied to all subsequent specimen images prior to analysis. Open a specimen image in the image analysis program and set the distance scale. Using the image analysis program, identify and define the boundaries of any printed color regions in the image of the specimen layer. Identification of color region boundaries should be performed with the intent of defining them as they would be discerned by a human viewer under standard lighting conditions with the unaided eye if the layer were being viewed face on in a flat configuration at approximately an arm's length distance. For example, intra-dot spaces commonly associated with ink-jet printing are included within that ink region, because they are perceived as part of that printed region by a typical viewer without magnification.

Calculate the area of each of the individual printed color regions within the image to the nearest 0.1 mm². Calculate the total area of printed color by summing up the areas of the individual printed color regions. Divide the total area of the printed color regions by the area of the entire specimen layer and multiply by 100. Record this value as the printed color percent area to the nearest 0.1%. In like fashion, analyze the remaining four specimen images. Calculate and report the average printed color percent area to the nearest 0.1% for the five replicates.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 10). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven substrate comprising a first surface and a second surface opposite the first surface; wherein the first surface comprises one or more printed portions, wherein at least one printed portion comprises a curable ink; and wherein the at least one printed portion comprises a Crosslinking Index of about 330 or less as determined by the Crosslinking Index Test Method herein and an Ink Adhesion Rating (Mineral Oil) of about 1.30 or greater as determined by the Ink Adhesion Rating Test Method herein.

2. The nonwoven substrate of claim 1 wherein the curable ink comprises an e-beam curable ink.

3. The nonwoven substrate of claim 2 wherein the at least one printed portion further comprises a Crosslinking Index of about 100 or less and/or an Ink Adhesion Rating (Mineral Oil) of about 2.5 or greater.

4. The nonwoven substrate of claim 1 wherein the curable ink comprises an UV-curable ink.

5. The nonwoven substrate of claim 4 wherein the at least one printed portion further comprises a Crosslinking Index of about 200 or less.

6. The nonwoven substrate of claim 1 wherein the curable ink comprises any of the colors of cyan, magenta, yellow, black and combinations thereof.

7. The nonwoven substrate of claim 1 wherein the curable ink is at least partially disposed in a graphic and/or pattern.

8. An article comprising a topsheet, backsheet, and absorbent core disposed between the topsheet and backsheet and a component comprising the nonwoven substrate of claim 1.

9. The nonwoven substrate of claim 1 wherein the at least one printed portion comprises an Ink Penetration Depth of about 250 microns or less.

10. The nonwoven substrate of claim 1 further comprising a basis weight of about 8 gsm to about 65 gsm.

11. The nonwoven substrate of claim 1 further comprising polyolefin fibers.

12. A nonwoven substrate comprising a first surface and a second surface opposite the first surface; wherein the first surface comprises a printed portion comprising a curable ink; wherein the printed portion comprises a Crosslinking Index of about 330 or less as determined by the Crosslinking Index Test Method herein and a $\Delta E^*$ of about 7 or greater as determined by the $\Delta E^*$ Determination Test Method herein.

13. The nonwoven substrate of claim 12 wherein the curable ink comprises an UV curable ink and the printed portion comprises a $\Delta E^*$ of from about 12 to about 50.

14. The nonwoven substrate of claim 12 wherein the curable ink comprises a Crosslinking Index of about 200 or less as determined by the Crosslinking Index Test Method herein.

15. The nonwoven substrate of claim 12 wherein the curable ink comprises an e-beam curable ink.

16. An article comprising a topsheet, backsheet and absorbent core disposed between the topsheet and backsheet and a component comprising the nonwoven substrate of claim 12.

17. A nonwoven substrate comprising a first surface and a second surface opposite the first surface; wherein the first surface comprises a printed portion comprising a curable ink; wherein the curable ink comprises a Crosslinking Index of about 330 or less, an Ink Adhesion Rating (Dry) of about 1.5 or greater, a $\Delta E^*$ of about 10 or greater, an Ink Penetration Depth of about 250 microns or less.

18. The nonwoven substrate of claim 17 wherein the curable ink comprises an e-beam ink.

19. The nonwoven substrate of claim 17 wherein the curable ink comprises a UV ink.

20. An article comprising a topsheet, backsheet and absorbent core disposed between the topsheet and backsheet and a component comprising the nonwoven substrate of claim 17.

\* \* \* \* \*